United States Patent
Hatayama et al.

(10) Patent No.: US 12,082,574 B2
(45) Date of Patent: *Sep. 10, 2024

(54) BIOMATERIAL PRESERVATION COMPOSITION HAVING A MICROBUBBLE WITH OXYGEN GAS IN LIQUID, METHOD FOR PRESERVING BIOMATERIAL IN THE BIOMATERIAL PRESERVATION COMPOSITION, METHOD FOR PRESERVING BIOMATERIAL IN THE BIOMATERIAL PRESERVATION COMPOSITION, METHOD FOR PRODUCING BIOMATERIAL USING THE BIOMATERIAL PRESERVATION COMPOSITION, TRANSPLANTATION MATERIAL USING THE BIOMATERIAL PRESERVATION COMPOSITION AND METHOD OF TRANSPLANTATION USING THE BIOMATERIAL PRESERVATION COMPOSITION

(71) Applicants: Aichi Medical University, Aichi (JP); Sumitomo Seika Chemicals Co., Ltd., Hyogo (JP)

(72) Inventors: Naoyuki Hatayama, Nagakute (JP); Munekazu Naito, Nagakute (JP); Shuichi Hirai, Nagakute (JP); Shigeki Sakaue, Hyogo (JP)

(73) Assignees: AICHI MEDICAL UNIVERSITY, Aichi (JP); SUMITOMO SEIKA CHEMICALS CO., LTD., Hyogo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 17/044,805

(22) PCT Filed: May 31, 2019

(86) PCT No.: PCT/JP2019/021855
§ 371 (c)(1),
(2) Date: Oct. 1, 2020

(87) PCT Pub. No.: WO2019/230973
PCT Pub. Date: Dec. 5, 2019

(65) Prior Publication Data
US 2021/0195887 A1 Jul. 1, 2021

(30) Foreign Application Priority Data
May 31, 2018 (JP) ................. 2018-105405
Dec. 3, 2018 (JP) ................. 2018-226902

(51) Int. Cl.
A01N 1/02 (2006.01)
(52) U.S. Cl.
CPC .................. A01N 1/021 (2013.01)
(58) Field of Classification Search
CPC .................................. A01N 1/021
See application file for complete search history.

(56) References Cited

U.S. PATENT DOCUMENTS

| | | | |
|---|---|---|---|
| 6,127,428 A * | 10/2000 | Lundgren | A61K 9/0026 514/743 |
| 2005/0260189 A1 | 11/2005 | Klibanov et al. | |
| 2008/0057486 A1 | 3/2008 | Mano et al. | |
| 2009/0130272 A1 | 5/2009 | Cutayar et al. | |
| 2009/0220644 A1 | 9/2009 | Vaslin et al. | |
| 2011/0208113 A1 | 8/2011 | Toma et al. | |
| 2014/0010848 A1* | 1/2014 | Kheir | A61K 9/5015 128/200.24 |
| 2016/0236158 A1 | 8/2016 | Bauer | |
| 2017/0056438 A1* | 3/2017 | Kamei | A01G 31/00 |
| 2019/0032006 A1 | 1/2019 | Kinooka et al. | |
| 2020/0009065 A1* | 1/2020 | Polizzotti | A61K 9/5192 |
| 2021/0137098 A1* | 5/2021 | Hatayama | A01N 1/021 |
| 2021/0244021 A1 | 8/2021 | Ohdaira | |
| 2022/0387333 A1* | 12/2022 | Hatayama | A61K 9/5089 |

FOREIGN PATENT DOCUMENTS

| | | |
|---|---|---|
| JP | H08-169801 A | 7/1996 |
| JP | 2001-259440 A | 9/2001 |
| JP | 2004-532623 A | 10/2004 |
| JP | 2008-063258 A | 3/2008 |
| JP | 2008-296096 A | 12/2008 |
| JP | 2009-044988 A | 3/2009 |
| JP | 2009-513121 A | 9/2009 |
| JP | 2010-517507 A | 5/2010 |
| JP | 2010-253405 A | 11/2010 |
| JP | 2011-047629 A | 3/2011 |
| JP | 2011-244779 A | 12/2011 |

(Continued)

OTHER PUBLICATIONS

Schreinemachers M-CJM, et al."Improved preservation and microcirculation with POLYSOL after transplantation in a porcine kidney autotransplantation mode" Nephrol Dial Transplant, 2009 (adv.pub. Oct. 10, 2008),24,pp. 816-824;doi: 10.1093/ndt/gfn559. (Year: 2008).*

Habran M, et al."IGL-1 preservation solution in kidney and pancreas transplantation: A systematic review" PLoS ONE,Apr. 2, 2020, 15(4),e0231019,12pages; https://doi.org/10.1371/journal.pone.0231019. (Year: 2020).*

Ramella SG, et al."Evaluation of a high sodium-low potassium cold-storage solution by the isolated perfused rat kidney technique" Nephrol Dial Transplant, 1995,75,pp. 842-846. (Year: 1995).*

Menasche P, et al."Experimental Evaluation of Celsior®, a New Heart Preservation Solution" Eur J Cadio-thorac Surg, 1994,8,pp .207-213. (Year: 1994).*

(Continued)

*Primary Examiner* — Aaron J Kosar
(74) *Attorney, Agent, or Firm* — Morgan, Lewis & Bockius LLP

(57) ABSTRACT

The present invention provides a composition that can preserve biomaterials. The biomaterial preservation composition of the present invention includes a micro bubble.

7 Claims, 11 Drawing Sheets

(56) References Cited

FOREIGN PATENT DOCUMENTS

| JP | 2014-161253 A | 9/2014 |
|---|---|---|
| JP | 2015-057951 A | 3/2015 |
| JP | 2015-174823 A | 10/2015 |
| JP | 2016-116492 A | 6/2016 |
| JP | 2016-536139 A | 11/2016 |
| JP | 2017-046648 A | 3/2017 |
| JP | 2017-056368 A | 3/2017 |
| JP | 2017-079610 A | 5/2017 |
| JP | 2018-521627 A | 8/2018 |
| JP | 2019-103958 A | 6/2019 |
| KR | 10-2014-0117214 * | 10/2014 |
| KR | 10-2014-0117214 A | 10/2014 |
| KR | 10-1658040 B1 | 9/2016 |
| WO | 02/070371 A2 | 9/2002 |
| WO | 2015/099201 A1 | 7/2015 |
| WO | WO 2015/099201 * | 7/2015 |
| WO | 2016/179483 A2 | 11/2016 |
| WO | 2017/082305 A1 | 5/2017 |
| WO | 2017/126647 A1 | 7/2017 |

OTHER PUBLICATIONS

Office Action issued in related Chinese Patent Application No. 201980036000.8 dated Aug. 13, 2021.
Government Public Relations Online, "Join us! Familiar volunteers who can save lives 'Blood Donation'," [online], search on May 31, 2018 <http://www.gov-online.go.jp/useful/article/201307/3.html#anc02>.
Japan Organ Transplant Network, "Organ Transplantation," [online], Search on May 31, 2018, <https://www.jotnw.or.jp/transplant/about.html>.
Nakao et al., "Ex vivo carbon monoxide prevents cytochrome P450 degradation and ischemia/reperfusion injury of kidney grafts," Kidney International, 74: 1009-1016 (2008).
Yoshida et al., "Ex vivo Application of Carbon Monoxide in UW Solution Prevents Transplant-Induced Renal Ischemia/Reperfusion Injury in Pigs," American Journal of Transplantation, 10: 763-772 (2010).
Nakao et al., "Ex Vivo Application of Carbon Monoxide in University of Wisconsin Solution to Prevent Intestinal Cold Ischemia/Reperfusion Injury," American Journal of Transplantation, 6: 2243-2255 (2006).
Kohmoto et al., "Carbon monoxide-saturated preservation solution protects lung grafts from ischemia-reperfusion injury," The Journal of Thoracic and Cardiovascular Surgery, 136 (4): 1067-1075 (2008).
Kaths et al., "Ex vivo machine perfusion for renal graft preservation," Transplantation Reviews, 32: 1-9 (2018).
International Search Report issued in corresponding International Patent Application No. PCT/JP2019/021855 dated Sep. 3, 2019.
Extended European Search Report issued in related/corresponding European Application No. 19812028.9 dated Apr. 8, 2022.
Extended European Search Report issued in related/corresponding European Application No. 19810847.4 dated Apr. 13, 2022.
Kay et al., "Ultrasonic microbubble contrast agents and the transplant kidney," Clinical Radiology, 64 (11): 1081-1087 (2009).
Fazekas et al., "Carboxyhemoglobin levels in medicalintensive care patients: a retrospective, observational study," Critical Care, 16 (1): R6 (2012).
Toffaletti et al., "Chapter Three—Monitoring Oxygen Status," Clinical Chemistry, 77: 106 [Advances in Clinical Chemistry, Edited by Gregory S.Makowski] (2016).
Deveci et al., "The measurement of exhaled carbon monoxidein healthy smokers and non-smokers," Respiratory Medicine, 98:551-556 (2004).
Mathur, "Use of Partial Recirculation to Limit Build-Up of Cabin Carbon Dioxide Concentrations to Safe Limits per ASHRAE Standard-62," SAE Technical Paper 2020-01-1245, pp. 1-10 [doi :10.4271/2020-01-1245] (2020).
Office Action issued in related Japanese Patent Application No. 2018-226900 dated Oct. 18, 2022.
Kraakman et al., "Review of mass transfer aspects forbiological gas treatment," Applied Microbiology and Biotechnology, 91 (4): 873-886 (2011).
Zhang et al., "The role of medical gas in stroke: an updated review," Medical Gas Research, 9 (4): 221-228 (2019).
Agarwal et al., "Principle and applications of microbubble and nanobubble technology for water treatment," Chemosphere, 84 (9): 1175-1180 (2011).
Office Action issued in corresponding/related Japanese Patent Application No. 2020-522643 dated Jan. 31, 2023.
Aili Sun et al., "Exogenous H2S modulates mitochondrial fusion-fission to inhibit vascular smooth muscle cell proliferation in a hyperglycemic state", Cell Biosci, 6:36, 1-18 (2016).
Yasuaki Kabe et al., "CO-responsive heme protein PGRMC1-mediated malignant tumor growth and Drug Resistance Mechanisms", Biochemistry, 89:6, 889-893 (2017).
Matteo Ciocci et al., "H2S-releasing nanoemulsions: a new formulation to inhibit tumor cells proliferation and improve tissue repair", Oncotarget, 7: 51, 84338-84358 (2016).
National Institute of Technology and Evaluation, Technical Support (Deposit of Patented Microorganisms). , 5 pages.
Tian Shuang et al., "The interaction of IGF-1/IGF-1R and hydrogen sulfide on the proliferation of mouse primary vascular smooth muscle cells", Biochemical Pharmacology, 149, 143-152 (2018).
Tokio Nei, "Preservation of Cells in Cryobiology", Japanese Journal of Freezing and Drying, 29, 53-58 (1983).
Traders Holdings: "A joint industry-university research project on the cold storage of organs and tissues has been started between a subsidiary and a company in which Traders Holdings has invested and the University of Tokyo", Feb. 7, 2018.
Yutao Yan, Ph.D et al., "CO suppresses prostate cancer cell growth by directly targeting LKB1/AMPK/mTOR pathway in vitro and in vivo", Urologic Oncology: Seminars and Original Investigations, Elsevier, 36:6, 312.e1-312.e8 (2018).
Azevedo et al., "Aqueous dispersions of nanobubbles: Generation, properties and features," Minerals Engineering, 94: 29-37 (2016).
Li et al., "Controllable CO-Release Following Near-Infrared Light-Induced Cleavage of Iron Carbonyl Derivatized Prussian Blue Nanoparticles for CO-Assisted Synergistic Treatment," ACS Nano (2016).
Alonso et al., "Carbon Monoxide Specifically Inhibits Cytochrome C Oxidase of Human Mitochondrial Respiratory Chain," Pharmacology & Toxicology, 93: 142-146 (2003).
Wegiel et al., "Carbon Monoxide Expedites Metabolic Exhaustion to Inhibit Tumor Growth," Cancer Research, 73 (23): 7009-7021 (2013).
Ushikubo et al., "Evidence of the existence and the stability of nano-bubbles in water," Colloids and Surfaces A: Physicochemical and Engineering Aspects, 361: 31-37 (2010).
Ohgaki et al., "Physicochemical approach to nanobubble solutions," Chemical Engineering Science, 65: 1296-1300 (2010).
Liu et al., "Effects of nanobubbles on the physicochemical properties of water: The basis for peculiar properties of water containing nanobubbles," Chemical Engineering Sciences, 93: 250-256 (2013).
Li et al., "Impact of Groundwater Salinity on Bioremediation Enhanced by Micro-Nano Bubbles," Materials, 6: 3676-3687 (2013).
Jiang et al., "Hydrogen Sulfide-Mechanisms of Toxicity and Development of an Antidote," Scientific Reports, 6: 20831 (2016).
Office Action issued in the related Japanese Patent Application No. 2022-193951, dated Jan. 30, 2024, 9 pages.

* cited by examiner

BIOMATERIAL PRESERVATION COMPOSITION HAVING A MICROBUBBLE WITH OXYGEN GAS IN LIQUID, METHOD FOR PRESERVING BIOMATERIAL IN THE BIOMATERIAL PRESERVATION COMPOSITION, METHOD FOR PRESERVING BIOMATERIAL IN THE BIOMATERIAL PRESERVATION COMPOSITION, METHOD FOR PRODUCING BIOMATERIAL USING THE BIOMATERIAL PRESERVATION COMPOSITION, TRANSPLANTATION MATERIAL USING THE BIOMATERIAL PRESERVATION COMPOSITION AND METHOD OF TRANSPLANTATION USING THE BIOMATERIAL PRESERVATION COMPOSITION

TECHNICAL FIELD

The present invention relates to a biomaterial preservation composition, a method for preserving a biomaterial, a method for producing a biomaterial, a transplantation material, and a method of transplantation.

BACKGROUND ART

Organ transplantation is performed to treat patients with impaired or failing functions of organs. However, since donors of organs for organ transplantation are mainly brain dead, the number of organs is insufficient (Non Patent Literature). For this reason, it has been attempted to use a cadaveric body as a supply source of an organ, to preserve the organ obtained from the cadaveric body, and then to transplant the organ.

However, since organs obtained from cadaveric bodies have different periods of time after death to obtain organs, there is a problem that damages to the organs tend to occur during reperfusion after transplantation, and the quality of the organs after preservation is not constant.

CITATION LIST

Non Patent Literature

Non Patent Literature 1: Japan Organ Transplant Network, "Organ Transplantation", [online], [Search on May 31, 2018], Internet <https://www.jotnw.or.jp/transplant/about.html>

SUMMARY OF INVENTION

Technical Problem

With the foregoing in mind, it is an object of the present invention to provide a composition that can preserve biomaterials.

Solution to Problem

In order to achieve the above object, the present invention provides a biomaterial preservation composition including a micro bubble.

The present invention also provides a method for preserving a biomaterial (hereinafter, also referred to as the "first preservation method", including the step of: preserving a biomaterial in a presence of a micro bubble.

The present invention also provides a method for preserving a biomaterial (hereinafter, also referred to as the "second preservation method", including the steps of: introducing a micro bubble into a biomaterial; and preserving the biomaterial.

The present invention also provides a method for producing a biomaterial (hereinafter, also referred to as the "production method", including the step of: preserving a produced biomaterial, wherein the material preserving step is performed by the method for preserving a biomaterial according to the present invention.

The present invention also provides a transplantation material produced by the method for producing a biomaterial according to the present invention.

The present invention also provides a method of transplantation, including the step of: transplanting the transplantation material according to the present invention into an animal.

Advantageous Effects of Invention

According to the composition of the present invention, biomaterials can be preserved.

COMPOSITION

Figure 1:
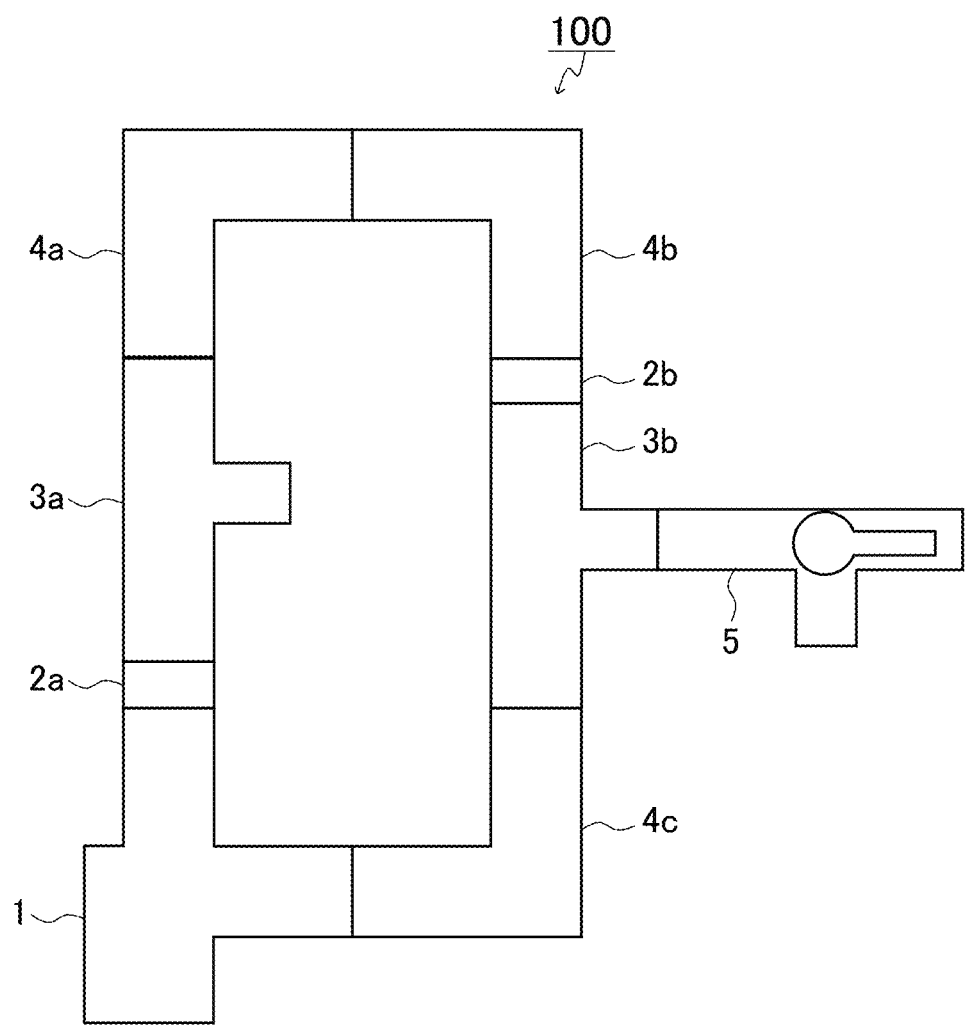
FIG. 1 is a schematic diagram showing an apparatus for producing micro bubbles in Reference Example 4.

The composition of the present invention includes a micro bubble, as described above. The composition of the present invention is characterized in that it includes a micro bubble, and other configurations and conditions are not particularly limited. According to the composition of the present invention, for example, although the mechanism is unknown, it is possible to suppress a decrease in viability of cells, to control the activation/inactivation of cells, and/or to control the metabolism during cell preservation (hereinafter also referred to as the "cell preservation effect"). According to the composition of the present invention, for example, although the mechanism is unknown, it is possible to suppress a damage to a biomaterial that occurs when a biomaterial after being preserved is reperfused. Therefore, according to the composition of the present invention, the biomaterial can be preserved in a state of capable of exhibiting its function even after preservation (hereinafter, also referred to as the "biomaterial preservation effect").

In the present invention, "micro bubble" means a closed minute space made of a gas surrounded by something other than the gas, and can also be referred to as, for example, a minute bubble. The micro bubble may be, for example, a fine bubble. The fine bubble generally means a micro bubble having a bubble diameter of less than 100 µm. The bubble diameter means a spherical equivalent diameter of the bubble. The bubble diameter may be a mean diameter (arithmetic mean diameter) of micro bubbles obtained by the measurement method to be described below. The fine bubble may be a microbubble or an ultrafine bubble. The microbubble generally means a micro bubble having a bubble diameter of 1 µm or more and less than 100 µm. The ultrafine bubble generally means a micro bubble having a bubble diameter of less than 1 µm.

The micro bubbles are present dispersed in a medium. The micro bubbles are present dispersed in whole or in part in the medium. In the latter case, it can be also said that the micro bubbles are localized to a part of the medium. The medium can be, for example, a liquid or a solid. Examples of the liquid include aqueous solvents containing water, oily solvents, and mixed solvents thereof. The liquid also includes a sol. Examples of the solid include solids obtained by coagulating the liquid. The solid also includes a gel. Regarding the liquid and the solid, for example, reference can be made to the description as to the object in the object production method of the present invention described below.

The micro bubbles may include any type of gas. Examples of the gas (gas component) include biogas such as carbon monoxide (CO), nitrogen monoxide (NO), hydrogen sulfide ($H_2S$), and hydrogen ($H_2$); rare gas such as helium (He), argon (Ar), krypton (Kr), and xenon (Xe); carbon dioxide ($CO_2$); oxygen ($O_2$); ozone ($O_3$); nitrous oxide ($N_2O$); carbon dioxide ($CO_2$); nitrogen ($N_2$); methane ($CH_4$); ethane ($CH_3CH_3$); propane ($CH_3CH_2CH_3$); fluoromethane ($CH_3F$); difluoromethane ($CH_2F_2$); carbon tetrafluoride ($CF_4$), ethylene oxide ($C_2H_4O$); and air. In the present application, the "biological gas" means a gas containing carbon monoxide (CO), nitric oxide (NO), hydrogen sulfide ($H_2S$), or hydrogen ($H_2$), or a mixed gas containing two or more of these. It is preferable that the micro bubbles contain at least one of CO and $H_2S$ so that the cell preservation effect and the biomaterial preservation effect can further be enhanced. The micro bubbles contain one or more types of gases. In the latter case, in the composition of the present invention, each micro bubble contains one or more types of gases. When the micro bubbles contain at least one of CO and $H_2S$, it is preferable that the micro bubbles contain $O_2$ so that the cell preservation effect and the biomaterial preservation effect can further be enhanced. The micro bubbles exclude a case where the gas is only air, for example. In the present invention, the "air" means, for example, air (atmosphere) used in producing the micro bubbles. It is preferable that the gas in the micro bubbles is a gas derived from a medical gas when it has a medical gas grade.

The density of the micro bubbles (micro bubble density) means the number of micro bubbles relative to the volume of the medium. The "density" can also be referred to as a number concentration. The lower limit of the micro bubble density is, for example, $5 \times 10^5$ bubbles/ml, $1 \times 10^6$ bubbles/ml, $5 \times 10^6$ bubbles/ml, $1 \times 10^7$ bubbles/ml, $5 \times 10^7$ bubbles/ml, $1 \times 10^8$ bubbles/ml, $5 \times 10^8$ bubbles/ml, or $1 \times 10^9$ bubbles/ml, and preferably $1 \times 10^6$ bubbles/ml, $5 \times 10^6$ bubbles/ml, $1 \times 10^7$ bubbles/ml, $5 \times 10^7$ bubbles/ml, $1 \times 10^8$ bubbles/ml, or $5 \times 10^8$ bubbles/ml. The upper limit of the micro bubble density is, for example, $1.5 \times 10^9$ bubbles/ml, $2 \times 10^9$ bubbles/ml, $3 \times 10^9$ bubbles/ml, $5 \times 10^9$ bubbles/ml, $7 \times 10^9$ bubbles/ml, $9 \times 10^9$ bubbles/ml, $1 \times 10^{10}$ bubbles/ml, $5 \times 10^{10}$ bubbles/ml, $1 \times 10^{11}$ bubbles/ml, $5 \times 10^{11}$ bubbles/ml, $1 \times 10^{12}$ bubbles/ml, or $5 \times 10^{12}$ bubbles/ml. The micro bubble density is, for example, in the range from $5 \times 10^5$ bubbles/ml to $5 \times 10^{12}$ bubbles/ml, $5 \times 10^5$ bubbles/ml to $1 \times 10^{12}$ bubbles/ml, $5 \times 10^5$ bubbles/ml to $5 \times 10^{11}$ bubbles/ml, $5 \times 10^5$ bubbles/ml to $1 \times 10^{11}$ bubbles/ml, $5 \times 10^5$ bubbles/ml to $5 \times 10^{10}$ bubbles/ml, $5 \times 10^5$ bubbles/ml to $1 \times 10^{10}$ bubbles/ml, $1 \times 10^6$ bubbles/ml to $9 \times 10^9$ bubbles/ml, $5 \times 10^6$ bubbles/ml to $9 \times 10^9$ bubbles/ml, $1 \times 10^7$ bubbles/ml to $7 \times 10^9$ bubbles/ml, $5 \times 10^7$ bubbles/ml to $7 \times 10^9$ bubbles/ml, $1 \times 10^8$ bubbles/ml to $5 \times 10^9$ bubbles/ml, $5 \times 10^8$ bubbles/ml to $5 \times 10^9$ bubbles/ml, $1 \times 10^9$ bubbles/ml to $3 \times 10^9$ bubbles/ml, $5 \times 10^8$ bubbles/ml to $2 \times 10^9$ bubbles/ml, or $5 \times 10^8$ bubbles/ml to $1.5 \times 10^9$ bubbles/ml.

The density, bubble diameter, and mean diameter (hereinafter also referred to as "characteristics") of the micro bubbles can be appropriately measured depending on the medium in which the micro bubbles are dispersed. When the micro bubbles are dispersed in a liquid medium, the characteristics of the micro bubbles can be calculated by analyzing the bubbles in the composition of the present invention by a particle tracking analysis method. The particle tracking analysis method can be performed, for example, using NanoSight® NS300 (manufactured by Malvern Instrument) according to Reference Example 4 to be described below. The characteristics of the micro bubbles may be calculated by an analysis method other than the particle tracking analysis method. In that case, the characteristics of the micro bubbles obtained by the other analysis method satisfy the above-mentioned examples when converted into the calculated value obtained by the particle tracking analysis method. When the micro bubbles are dispersed in a solid medium, the characteristics of the micro bubbles can be calculated based on the characteristics of the micro bubbles in the liquid before solidification of the medium and the characteristics of the micro bubbles in the liquid obtained by dissolving the solid medium.

When the gas contains CO, the proportion of CO in the gas is, for example, greater than 0%, 100% or less, 10 to 90%, 10 to 80%, 15 to 70%, 20 to 60%, 20 to 50%, or 20 to 40%, and preferably 20 to 30%.

When the gas contains $H_2S$, the proportion of $H_2S$ in the gas is, for example, greater than 0%, 100% or less, 10 to 90%, 10 to 80%, 15 to 70%, 20 to 60%, 20 to 50%, or 20 to 40%, and preferably 20 to 30%.

When the gas contains $O_2$, the proportion of $O_2$ in the gas is, for example, greater than 0%, less than 100%, 10 to 90%, 20 to 90%, 30 to 90%, 40 to 85%, 50 to 85%, or 60 to 85%, and preferably 70 to 80%.

When the gas contains CO and $O_2$, the volume ratio ($V_{CO}:V_{O2}$) between the volume ($V_{CO}$) of carbon monoxide and the volume ($V_{O2}$) of oxygen is, for example, 1:9 to 9:1. The volume ratio ($V_{CO}:V_{O2}$) is preferably 1.5:8.5 to 2.5:7.5 or 2:8 to 3:7 so that a decrease in viability of cells can be suppressed during cell preservation or cell culture to be described below and the biomaterial can be preserved in a state of capable of exhibiting its function. The volume ratio ($V_{CO}:V_{O2}$) is, for example, excluding the volume ratio ($V_{CO}:V_{O2}$) in the air.

When the gas contains $H_2S$ and $O_2$, the volume ratio ($V_{H2S}:V_{O2}$) between the volume ($V_{H2S}$) of hydrogen sulfide and the volume ($V_{O2}$) of oxygen is, for example, from 1:9 to 9:1. The volume ratio ($V_{CO}:V_{O2}$) is preferably 1.5:8.5 to 2.5:7.5 or 2:8 to 3:7 so that a decrease in viability of cells can be suppressed during cell preservation or cell culture to be described below and the biomaterial can be preserved in a state of capable of exhibiting its function. The volume ratio ($V_{H2S}:V_{O2}$) is, for example, excluding the volume ratio ($V_{H2S}:V_{O2}$) in the air.

The composition of the present invention can be produced, for example, by a method for producing a micro bubble such as fine bubble using a freely selected gas. For this reason, the method for producing a composition of the present invention includes, for example, the step of producing a micro bubble using a freely selected gas and a medium. As a specific example, when the composition of the present invention is a liquid, the liquid composition can be produced by using, for example, a freely selected gas, the medium, and a micro bubble production apparatus of a swirling flow type, an ejector type, a venturi type, a static mixer type, a micro-pore type, a pressure melting type, or an ultrasonic cavitation type. In addition, when the composition of the present invention is a solid, the solid composition can be produced by coagulating the composition of the liquid by a known method. When the solid is a gel, the gel composition can be produced, for example, by mixing the liquid composition with a gelling agent. At the start of the bubble producing step, the freely selected gas is in a state of a gas, a liquid, or a solid. The composition of the present invention can be produced, for example, by the object production method of the present invention described below. Regarding the freely selected gas, reference can be made to the description as to gases described above. The freely selected gas may be a plurality of types of gases. In this case, each gas may be separately subjected to the bubble producing step, or all or a part of the freely selected gas may be simultaneously subjected to the bubble producing step. As a specific example, when the gas includes CO and $O_2$, the CO and $O_2$ may be introduced simultaneously or separately.

The composition of the present invention may include other components such as, for example, a surfactant. Examples of the surfactant include ionic surfactants such as an anionic surfactant, a cationic surfactant, and an amphoteric surfactant; and nonionic surfactants. Examples of the anionic surfactant include monoalkyl anionic surfactants such as sodium lauryl sulfate and the like. Examples of the cationic surfactant include dialkyl cationic surfactants such as dimethyldioctadecylammonium chloride and the like. Examples of the nonionic surfactant include ether type nonionic surfactants such as octylphenol ethoxylate and the like. The composition of the present invention can improve the micro bubble density by including, for example, a surfactant, preferably a cationic surfactant.

The composition of the present invention can preserve a biomaterial as described above. For this reason, the composition of the present invention can be suitably used as, for example, a biomaterial preservation composition.

<Biomaterial Preservation Composition>

The biomaterial preservation composition of the present invention includes a micro bubble as described above. The biomaterial preservation composition of the present invention is characterized in that it includes a micro bubble, and other configurations and conditions are not particularly limited. According to the composition of the present invention, for example, although the mechanism is unknown, it is possible to suppress a damage to a biomaterial that occurs when a biomaterial after being preserved is reperfused. Therefore, according to the biomaterial preservation composition of the present invention, the biomaterial can be preserved in a state of capable of exhibiting its function even after preservation. According to the biomaterial preservation composition of the present invention, for example, the method for preserving a biomaterial and method for producing a biomaterial of the present invention described below can be easily performed. Regarding the biomaterial preservation composition of the present invention, for example, reference can be made to the description as to the composition of the present invention described above.

In the present invention, the "biomaterial" may be, for example, a part of a living body or an organ. Examples of a part of the living body include a limb, a finger, a face, a bone, a muscle, a hair root, a tooth, and a periodontal membrane. Examples of the organ include an eyeball, a cornea, a lung, a heart, a liver, a kidney, a spleen, a pancreas, a gall bladder, an esophagus, a stomach, a small intestine, a large intestine, a testis, an ovary, a central nervous system, a peripheral nervous system, a blood vessel, and skin. The biomaterial may be, for example, a biomaterial isolated from a living body or from a cadaveric body, or may be a biomaterial prepared by differentiating and inducing from cells such as stem cells, pluripotent including embryonic stem (ES) cells and induced pluripotent stem (iPS) cells, and the like. The biomaterial excludes, for example, isolated cells, cell sheets, and cell components. The cell sheet includes, for example, a laminate in which one or more kinds of cell sheets are laminated.

The biomaterial is derived from an animal, for example. The animal is not particularly limited, and examples thereof include humans and non-human animals excluding humans. Examples of the non-human animal include mammals such as a mouse, a rat, a guinea pig, a dog, a cat, a monkey, a rabbit, a sheep, a horse, a pig, and the like; and non-mammals such as a fly and the like.

In the biomaterial preservation composition of the present invention, the "biomaterial preservation" means, for example, keeping a biomaterial in a state as it is, and keeping the biomaterial in a state of capable of exhibiting its function at the time of use after preservation, and may mean either of them.

In the biomaterial preservation composition of the present invention, the micro bubbles may include any type of gas. Regarding the gas, for example, reference can be made to the description as to a gas (gas component) in the composition of the present invention described above. It is preferable that the micro bubbles contain at least one of CO and $H_2S$ so that a decrease in viability of cells can be further suppressed during cell preservation and the biomaterial can be preserved in a state of capable of exhibiting its function. The micro bubbles contain one or more types of gases. In the latter case, in the biomaterial preservation composition of the present invention, each micro bubble contains one or more types of gases. When the micro bubbles contain at least one of CO and $H_2S$, it is preferable that the micro bubbles contain $O_2$ so that a decrease in viability of cells can be further suppressed during cell preservation and the biomaterial can be preserved in a state of capable of exhibiting its function. The micro bubbles exclude a case where the gas is only air, for example. It is preferable that the gas in the micro bubbles is a gas derived from a medical gas when it has a medical gas grade.

In the biomaterial preservation composition of the present invention, the micro bubbles are present dispersed in a medium. The medium can be, for example, a liquid or a solid. Regarding the liquid and the solid, for example, reference can be made to the description as to the composition of the present invention and the description as to the object in the object production method of the present invention described below.

In the biomaterial preservation composition of the present invention, regarding the characteristics of the micro bubbles, the proportion of CO, $H_2S$, or $O_2$, the volume ratio ($V_{CO}$:$V_{O2}$), the volume ratio ($V_{H2S}$:$V_{O2}$), the production method, and the like, for example, reference can be made to the description as to the composition of the present invention described above.

The biomaterial preservation composition of the present invention may include other components. Examples of the other components include common components used for preserving biomaterials or cells, and examples thereof include buffering agents; nutritional components such as amino acids, sugars, vitamins, and the like; proteins such as growth factors, and the like; cryopreserving agents such as DMSO, and the like; salts; blood components such as serum, plasma, and the like; and the surfactants. The other components may include, for example, a preservation solution of a known biomaterial. Examples of the preservation solution include a University of Wisconsin (UW) solution, a histidine-tryptophan-ketoglutarate (HTK) solution, a preservation solution sold under the tradename CELSOIR, a ET-Kyoto solution, a preservation solution sold under the tradename IGL-1, a preservation solution sold under tradename POLYSOL, and Euro-Collins (EC) solution.

<Method for Producing Object Including Micro Bubbles>

The method for producing an object including a micro bubble of the present invention includes the step of introducing a micro bubble into an object as described above. The object production method of the present invention is characterized in that it includes the introducing step, and other steps and conditions are not particularly limited. According to the object production method of the present invention, for example, although the mechanism is unknown, it is possible to produce an object capable of suppressing a decrease in viability of cells during cell preservation described below. According to the object production method of the present invention, for example, although the mechanism is unknown, it is possible to produce an object in which a damage to a biomaterial that occurs when a biomaterial after being preserved is reperfused is suppressed. According to the method for producing an object of the present invention, for example, it is possible to produce a composition of the present invention. Thus, the method for producing an object of the present invention can also be referred to as a method for producing a composition of the present invention. Regarding the method for producing an object of the present invention, for example, reference can be made to the description as to the composition and the biomaterial preservation composition of the present invention described above.

In the introducing step, micro bubbles are introduced into the object. In the introducing step, the physical properties of the object may be a liquid or a solid. The liquid includes a sol and the solid includes a sol. Examples of the object include an aqueous solvent such as water; an oily solvent; a preservative solution such as a physiological saline, a University of Wisconsin (UW) solution, a histidine-tryptophan-ketoglutarate (HTK) solution, a preservation solution sold under the tradename CELSOIR, a ET-Kyoto solution, a preservation solution sold under the tradename POLYSOL, a Euro-Collins solution, or the like; an extracellular solution (infusion) such as a solution sold under the trade names LACTEC D, VIENNA F, SOLUGEN D, or SOLLACTO, lactrine gel, or the like; and a mixed solvent thereof.

In the introducing step, a method for introducing micro bubbles into the object may be performed as follows. That is, micro bubbles may be introduced using the object and a freely selected gas, or the micro bubbles may be introduced by bringing the object into contact with or mixing the object with a medium containing the micro bubbles, for example. In the former case, the introducing step can be performed, for example, in the same manner as in the bubble producing step in the composition of the present invention. In the latter case, the introducing step can be performed, for example, by bringing the object into contact with or mixing the object with the composition of the present invention. Since the introducing step can further enhance the cell preservation effect or the biomaterial preservation effect, it is preferable to introduce the micro bubbles using at least one of CO and $H_2S$. In addition, in the introducing step, when micro bubbles are introduced using at least one of CO and $H_2S$, since the introducing step can further enhance the cell preservation effect or the biomaterial preservation effect, it is preferable to introduce the micro bubbles using $O_2$. The micro bubbles exclude a case where the gas is only air, for example. It is preferable that the gas in the micro bubbles is a gas derived from a medical gas when it has a medical gas grade.

The gas to be introduced into the object is a freely selected gas. Regarding the freely selected gas, reference can be made to the description as to a gas (gas component) in the composition of the present invention described above. The freely selected gas may be a plurality of types of gases. When micro bubbles containing a plurality of types of gases are introduced into the object, one or more types of gases may be separately introduced or a plurality of types of gases may be simultaneously introduced into the object. As a specific example, when the gas is CO and $O_2$, the CO and $O_2$ may be introduced simultaneously or separately. The gas to be introduced into the object excludes a case where the gas is only air, for example. It is preferable that the gas in the micro bubbles is a gas derived from a medical gas when it has a medical gas grade.

In the introducing step, regarding the characteristics of the micro bubbles to be introduced into the object, the gas concentration, the proportion of CO, $H_2S$, or $O_2$, the volume ratio ($V_{CO}$:$V_{O2}$), the production method, and the like, for example, reference can be made to the description as to the composition of the present invention described above.

The introducing step may be performed, for example, in the presence of a surfactant. By carrying out the introducing step in the presence of a surfactant, it is possible to improve the density of micro bubbles in the obtained object.

The introducing step may be performed, for example, in the presence of a surfactant. By carrying out the introducing step in the presence of a surfactant, it is possible to improve the density of microbubbles in the obtained object.

<First Method for Preserving Biomaterial>

The method for preserving a biomaterial of the present invention includes the step of preserving a biomaterial in the presence of a micro bubble, as described above. The first preservation method of the present invention is characterized in that it includes the step of preserving a biomaterial in the presence of a micro bubble, and other steps and conditions are not particularly limited. According to the first preservation method of the present invention, for example, it is possible to suppress a damage to a biomaterial that occurs when a biomaterial after being preserved is reperfused. Therefore, according to the first preservation method of the present invention, the biomaterial can be preserved in a state of capable of exhibiting its function even after preservation. Regarding the first preservation method of the present invention, for example, reference can be made to the description as to the composition, the biomaterial preservation composition, and the object production method of the present invention described above.

In the preserving step, biomaterials are preserved in the presence of micro bubbles. Specifically, in the preserving step, biomaterials are preserved in the presence of a medium containing the micro bubbles. Regarding the medium, for example, reference can be made to the description as to the medium in the composition of the present invention and the description as to the object in the object production method of the present invention described above. As a specific example, in the preserving step, a liquid containing the biomaterials (for example, a liquid in which the biomaterial is immersed) and a medium containing the micro bubbles may be brought into contact or mixed and the obtained mixture may be preserved, or the biomaterials and a medium containing the micro bubbles may be brought into contact or mixed and the obtained mixture may be preserved. The preservation method in the preserving step can be performed by a known method such as a simple immersion preservation method, a continuous perfusion preservation method, a vapor phase preservation method, or the like, for example. Regarding the vapor phase preservation method, for example, reference can be made to JP 2015-174823A. In addition, in the preserving step, the biomaterial may be preserved by continuously perfusing the biomaterial with a medium containing the micro bubbles.

In the preserving step, the preservation condition for preserving the biomaterials can be, for example, based on the type of the biomaterials and known culture conditions. As a specific example, when the medium is a liquid and atmospheric pressure is at normal pressure (about 1013 hPa), the preservation temperature of the biomaterial is, for example, 0° C. to 37° C. or 4° C. to 37° C. The preservation period is, for example, 0 to 7 days or 1 to 7 days. In the preserving step, when the kidney as the biomaterial is preserved in a continuous perfusion manner by a medium containing the micro bubbles, the perfusion rate of the medium is, for example, 60 bpm (Beats Per Minute). The upper and lower limits of pressure at the time of perfusion are, for example, 30 mmHg and 20 mmHg, or 60 mmHg and 40 mmHg, respectively. The vascular resistance at the time of perfusion is, for example, 0.25 mmHg/ml/min or less.

In the first preservation method of the present invention, the micro bubbles may include a freely selected gas as a gas. Regarding the freely selected gas, for example, reference can be made to the description as to a gas (gas component) in the composition of the present invention described above. It is preferable that the micro bubbles contain at least one of CO and $H_2S$ so that a decrease in viability of cells can be further suppressed during cell preservation and the biomaterial can be preserved in a state of capable of exhibiting its function. The micro bubbles contain one or more types of gases. In the latter case, in the first preservation method of the present invention, each micro bubble contains one or more types of gases. When the micro bubbles contain at least one of CO and $H_2S$, it is preferable that the micro bubbles contain $O_2$ so that a decrease in viability of cells can be further suppressed during cell preservation and the biomaterial can be preserved in a state of capable of exhibiting its function. The micro bubbles exclude a case where the gas is only air, for example. It is preferable that the gas in the micro bubbles is a gas derived from a medical gas when it has a medical gas grade.

In the first preservation method of the present invention, regarding the characteristics of the micro bubbles, the gas concentration, the proportion of CO, $H_2S$, or $O_2$, the volume ratio ($V_{CO}:V_{O2}$), the volume ratio ($V_{H2S}:V_{O2}$), the production method, and the like, for example, reference can be made to the description as to the composition and the object production method of the present invention described above.

It is preferable that the first preservation method of the present invention includes the step of perfusing a biomaterial with a liquid containing the micro bubbles so that a damage to the biomaterial that occurs when a biomaterial after being preserved can be reperfused. The perfusing step is performed prior to the preserving step, for example. In the perfusing step, a method for perfusing a biomaterial using the liquid can be performed by a known method such as a simple perfusion method or a mechanical perfusion method, for example, depending on the type of the biomaterial. As a specific example, when the biomaterial has a blood vessel or a lymphatic vessel, the perfusing step may be performed, for example, by introducing a liquid containing the micro bubbles into the blood vessel or lymphatic vessel. After the perfusing step, in the preserving step, as described above, the biomaterial may be immersed in a liquid containing the micro bubbles to preserve (a simple immersion method), or the biomaterial may be preserved by continuously or discontinuously perfusing the biomaterial with a liquid containing the micro bubbles using a perfusion device or the like (a continuous perfusion method), or the biomaterial may be preserved in the presence of a high pressure gas (a vapor phase preservation method). As a method for preserving in the presence of the high pressure gas, for example, reference can be made to the method described in JP2015-174823A. Regarding the liquid, for example, reference can be made to the description as to a medium in the composition of the present invention and the description as to the object in the object production method of the present invention.

<Second Method for Preserving Biomaterial>

The method for preserving a biomaterial of the present invention includes: the steps of introducing a micro bubble into a biomaterial; and the step of preserving the biomaterial, as described above. The second preservation method of the present invention is characterized in that it includes the step of introducing a micro bubble into a biomaterial, and other steps and conditions are not particularly limited. According to the second preservation method of the present invention, for example, it is possible to suppress a damage to a biomaterial that occurs when a biomaterial after being preserved is reperfused. Therefore, according to the second preservation method of the present invention, the biomaterial can be preserved in a state of capable of exhibiting its function even after preservation. Regarding the second preservation method of the present invention, for example, reference can be made to the description as to the composition, the biomaterial preservation composition, the object production method, and the first preservation method of the present invention described above.

In the introducing step, micro bubbles are introduced into the biomaterial. Specifically, the introducing step can be performed by bringing the biological material and the medium containing the micro bubbles into contact with each other, for example. Regarding the medium, for example, reference can be made to the description as to the medium in the composition of the present invention and the description as to the object in the object production method of the present invention. The medium containing the micro bubbles may be brought into contact with the surface of the biomaterial, the medium containing the micro bubbles may be brought into contact with the inside of the biomaterial, or the medium containing the micro bubbles may be brought into contact with the surface and the inside of the biomaterial. It is preferable that the medium containing the micro bubbles be brought into contact with the inside of the biomaterial so that a damage to the biomaterial that occurs when a biomaterial after being preserved is reperfused can be suppressed by introducing micro bubbles into the entire biomaterial. When the medium containing the micro bubbles is brought into contact with the surface of the biomaterial, for example, the introducing step may be performed by washing the biomaterial with a medium containing the micro bubbles. When the medium containing the micro bubbles is brought into contact with the inside of the biomaterial, for example, the introducing step may be performed by perfusing the biomaterial with a liquid containing the micro bubbles. Regarding the perfusion, for example, reference can be made to the description as to the perfusing step in the first preservation method of the present invention, and can be performed utilizing a circulation system such as a blood vessel or a lymphatic vessel. In addition, when the medium containing the micro bubbles is brought into contact with the surface and the inside of the biomaterial, for example, the introducing step can be performed by immersing the biomaterial in a medium containing the micro bubbles. The immersion time in the medium is, for example, 1 minute to 6 hours. The temperature at the time of immersion in the medium is, for example, 0 to 37° C. or 4 to 37° C.

The introducing step may be performed on an isolated biomaterial or on a biomaterial before isolation. When the introducing step is performed on the biomaterial after isolation, the introducing step can be performed by bringing the isolated biomaterial into contact with a medium containing the micro bubbles. When the introducing step is performed on the biomaterial before isolation, the introducing step can be performed by introducing micro bubbles into an animal having a biomaterial to be introduced with micro bubbles. Specifically, the introducing step may be performed, for example, by administering to the animal a medium containing micro bubbles. Examples of the route of administration to the animal include topical administration, enteral administration, and parenteral administration. Examples of the topical administration include skin administration, inhalation administration, enema administration, eye drop, ear drop, nasal administration, and vaginal administration. Examples of the enteral administration include oral administration, tube feeding, and enema administration. Examples of the parenteral administration include intravenous administration, transarterial administration, intramuscular administration, intracardiac administration, subcutaneous administration, intraosseous administration, intradermal administration, intraperitoneal administration, intrathecal administration, intravesical administration, transdermal administration, and inhalation administration.

When the introducing step is performed on a biomaterial before isolation, it is preferable that the second preservation method of the present invention further includes the step of isolating a biomaterial after the introducing step, for example. In the isolating step, the method for isolating the biomaterial can be appropriately determined, for example, depending on the type of the biomaterial.

Next, in the preserving step, the biomaterial is preserved. The biomaterial may be preserved in the presence of the micro bubbles or may be performed in the absence of the micro bubbles, for example. When the preserving step is performed in the presence of the micro bubbles, the preserving step can be performed in the same manner as the preserving step in the first preservation method of the present invention, for example. When the preserving step is performed in the absence of the micro bubbles, the preserving step may be performed by a known preservation method such as, for example, a simple immersion preservation method, a continuous perfusion preservation method, a vapor phase preservation method, or the like. Regarding the vapor phase preservation method, for example, reference can be made to JP 2015-174823A described above. In addition, in the preserving step, the biomaterial may be preserved by continuously perfusing the biomaterial with a medium containing the micro bubbles.

In the second preservation method of the present invention, regarding the characteristics of the micro bubbles, the gas concentration, the proportion of CO, $H_2S$, or $O_2$, the volume ratio ($V_{CO}:V_{O2}$), the volume ratio ($V_{H2S}:V_{O2}$), the production method, and the like, for example, reference can be made to the description as to the composition and the object production method of the present invention described above.

The second preservation method of the present invention may include the step of perfusing the biomaterial with a liquid after the introducing step, for example. The liquid is, for example, a liquid containing sugar, and specific examples thereof include the preservation liquid and the like. The liquid may not contain micro bubbles.

<Method for Producing Biomaterial>

The method for producing a biomaterial of the present invention includes the step of preserving a produced biomaterial, wherein the material preserving step is performed by the method for preserving a biomaterial of the present invention, as described above. The production method of the present invention is characterized in that the material preserving step is performed by the method for preserving a biomaterial of the present invention, and other steps and conditions are not particularly limited. According to the production method of the present invention, it is possible to produce a biomaterial in which a damage to a biomaterial that occurs when a biomaterial after being preserved is reperfused is suppressed, for example. Therefore, according to the production method of the present invention, for example, it is possible to produce a biomaterial in a state of capable of exhibiting its function even after preservation. Regarding the preservation method of the present invention, for example, reference can be made to the description as to the composition, the biomaterial preservation composition, the object production method, and the preservation method of the present invention.

The material preserving step can be performed by the preservation method of the present invention, as described above, and reference can be made to the description as to the preservation method of the present invention. The preservation method of the present invention may be the first preservation method of the present invention or the second preservation method of the present invention. When the material preserving step is performed by the first preservation method of the present invention, it is preferable that the production method of the present invention includes the introducing step of introducing micro bubbles into the biomaterial so that a damage to a biomaterial that occurs when a biomaterial after being preserved is reperfused can be further suppressed, for example. Regarding the introducing step, for example, reference can be made to the description as to the introducing step in the second preservation method of the present invention. It is preferable that the introducing step includes the step of perfusing the biomaterial with a liquid containing the micro bubbles. Regarding the perfusing step, for example, reference can be made to the description as to the perfusing step in the first preservation method of the present invention.

<Transplantation Material>

The transplantation material of the present invention is produced in the biomaterial production method of the present invention as described above. The transplantation material of the present invention is characterized in that it is produced by the biomaterial production method of the present invention, and other configurations and conditions are not particularly limited. The transplantation material of the present invention can suppress a damage to a transplantation material that occurs when a biomaterial after being preserved is reperfused. Therefore, according to the transplantation material of the present invention, for example, a transplantation material is preserved in a state of capable of exhibiting its function even after preservation, and it functions well even after transplantation. Further, according to the transplantation material of the present invention, for example, it is possible to reduce the time for preconditioning the transplantation material. Regarding the transplantation material of the present invention, for example, reference can be made to the description as to the composition, the biomaterial preservation composition, the object production method, the preservation method, and the production method of the present invention.

<Transplantation Method>

The transplantation method of the present invention includes the step of transplanting the transplantation material of the present invention into an animal. The transplantation method of the present invention is characterized in that it includes the step of transplanting the transplantation material of the present invention into an animal, and other steps and conditions are not particularly limited. The transplantation material used in the transplantation method of the present invention can suppress a damage to a transplantation material that occurs when a transplantation material after being preserved is reperfused, for example. For this reason, the transplantation material used in the transplantation method of the present invention is preserved in a state of capable of exhibiting its function even after preservation. Therefore, according to the transplantation method of the present invention, the transplantation material functions well even after transplantation. Further, according to the transplantation method of the present invention, for example, it is possible to reduce the time for preconditioning the transplantation material. Regarding the transplantation method of the present invention, for example, reference can be made to the description as to the composition, the biomaterial preservation composition, the object production method, the preservation method, the production method, and the transplantation material of the present invention.

In the transplanting step, the animal is not particularly limited, and examples thereof include humans and non-human animals excluding humans. Examples of the non-human animal include mammals such as a mouse, a rat, a guinea pig, a dog, a cat, a monkey, a rabbit, a sheep, a horse, a pig, and the like; and non-mammals such as a fly and the like. In the transplanting step, the type of the animal and the origin of the transplantation material after preservation may be the same or different.

The transplantation method of the present invention may further include the step of washing the transplantation material with a washing liquid prior to the transplanting step. In this case, the transplanting step may be a step of transplanting the transplantation material after being washed into the animal. The washing step is a step of washing the transplantation material after being preserved with a washing liquid, thereby reducing the amount of the preservation liquid contained in the transplantation material after preservation, for example. The transplantation method of the present invention includes the washing step, and thus, for example, when the transplantation material is transplanted, side effects due to the preservation liquid to the transplanted animal can be further reduced.

Examples of the washing liquid include physiological saline, phosphate buffered saline, and a Ringer's solution.

In the transplanting step, the method of transplantation of the transplantation material after preservation is not particularly limited, and can be appropriately determined depending on the transplantation material after preservation. Regarding the transplantation method, for example, reference can be made to the following Reference 1.

Reference 1: "Organ Transplantation Experimental Manual: Model of Transplantation and Ischemia-Reperfusion Injury Using Rats and Mice"; Shujunsha Co., Ltd., Supervised by Masumi Nozawa; Edited by Yayoi Tanaka, 1999.

<Micro Bubble Density Improver>

The micro bubble density improver of the present invention (hereinafter, also referred to as the "improver") includes a surfactant as an active ingredient. The micro bubble density improver of the present invention is characterized in that it includes a surfactant as an active ingredient, and other configurations and characteristics are not particularly limited. According to the improver of the present invention, when a medium containing micro bubbles is produced, the density of micro bubbles in the obtained product can be improved. Regarding the improver of the present invention, for example, reference can be made to the description as to the composition, the biomaterial preservation composition, and the object production method of the present invention described above.

The dosage form of the improver of the present invention is not particularly limited, and examples thereof include tablets, liquids, granules, and powders. The improver of the present invention may include components other than a surfactant. In this case, the improver of the present invention can also be referred to as, for example, a micro bubble density improving composition.

EXAMPLES

Next, examples of the present invention will be described. The present invention, however, is not limited to the examples below.

Reference Example 4

It was examined that the biomaterial preservation composition of the present invention can preserve cells.

(1) Production of Composition

A composition of the present invention was produced using a venturi type micro bubble production apparatus 100 shown in FIG. 1. As shown in FIG. 1, the production apparatus 100 has a circulation system flow path in which a tube 2a, a venturi tube 3a, connecting tubes 4a and 4b, a tube 2b, a venturi tube 3b, and a connecting tube 4c are connected in this order to communicate with each other with reference to a motor 1. An opening formed in a protrusion of the side surface of the venturi tube 3a is sealed. Further, an opening formed in a protrusion of the side surface of the venturi pipe 3b is connected to a three-way stopcock 5 so as to communicate with each other. First, the three-way stopcock 5 was opened, and a DMEM medium was introduced from the three-way stopcock 5 into the flow path in the production apparatus 100. At this time, the flow path was filled with the DMEM medium so as not to contain a gas. The liquid amount of the filled DMEM medium was also measured. Next, carbon monoxide (CO concentration: 99.999 (v/v) %, manufactured by Sumitomo Seika Chemicals Co., Ltd.) and medical oxygen ($O_2$ concentration: 99.999 (v/v) %, manufactured by Sumitomo Seika Chemicals Co., Ltd.) were introduced into the flow path so as to be about 20 ml with respect to 100 ml of the introduced DMEM medium (about 10 ml gas/50 ml solvent (DMEM medium)), and the three-way stopcock 5 was closed. The volume ratio ($V_{CO}:V_{O2}$) of carbon monoxide and oxygen introduced into the flow path was 10:0, 9:1, 8:2, 7:3, 6:4, 5:5, 4:6, 3:7, 2:8, 1:9, or 0:10. Then, by circulating DMEM medium water and air in the flow path for 5 to 10 minutes using the motor 1, micro bubbles were formed, thereby producing a composition. The flow rate at which DMEM medium was circulated by the motor 1 was 3.6 l/min.

(2) Characteristics of Composition

The physical properties of the composition obtained by Reference Example 4 (1) described above were measured using NanoSight® NS300 (manufactured by Malvern Instrument) with a default parameter after being stand for about 2 hours. The measurement was performed at 25° C. As a result, the mean diameter of the micro bubbles in the composition was 114.8 nm, and the density of the micro bubbles in the composition was $6.46 \times 10^8$ bubbles/ml.

(3) Cell Preservation

A cell suspension of rat cardiac rhabdomyocytes (H9c2 cells, obtained from Hamamatsu University School of Medicine) was seeded in a 96-well dish so as to achieve 80% confluent/well and cultured for 1 to 2 days. The composition of the medium was such that 10% FBS (fetal bovine serum) was added to the composition. The culture condition was 37° C. and 5% $CO_2$. The micro bubble density in the culture solution after adding 10% FCS is estimated to be $5.81 \times 10^8$ bubbles/ml.

After the addition, the dish was preserved for 24 hours at 4° C. Further, after the culture at 37° C. and 5% $CO_2$ for 1 hour, the viability of cells was examined by measuring the absorbance of each well using a MTT assay kit (CellTiter 96® AQueous One Solution Cell Proliferation Assay, manufactured by Promega Corporation) based on the attached protocol. As a Control, the measurement was performed in the same manner as described above except that 10% FCS-containing DMEM medium was used. The results are shown in FIG. 2.

Figure 2:
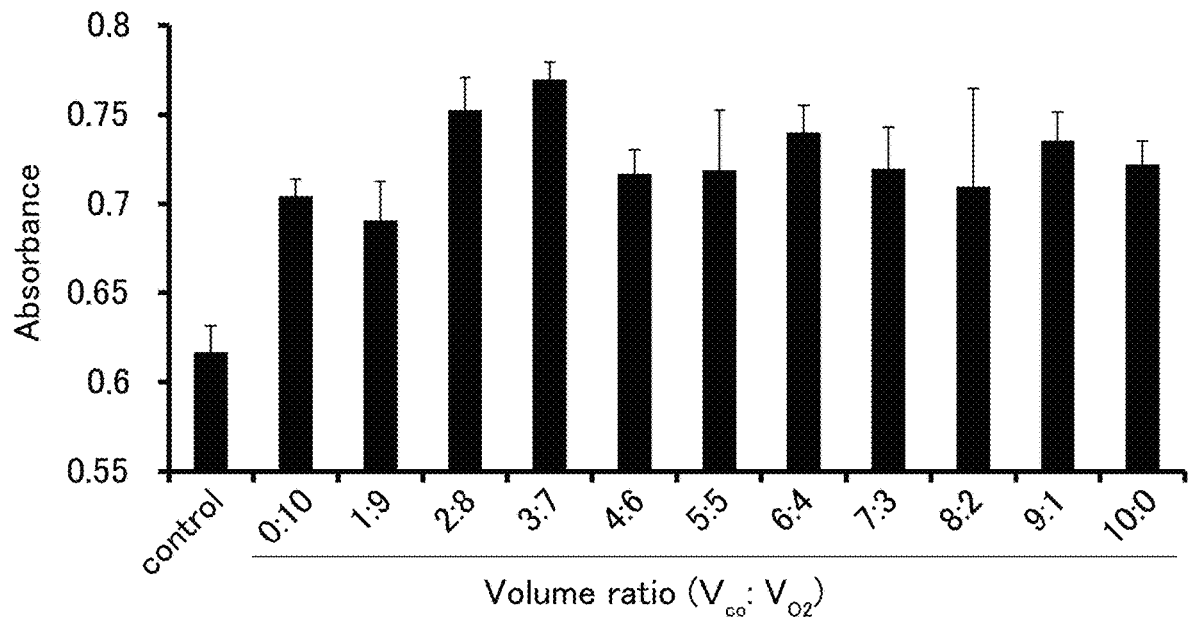
FIG. 2 is a graph showing the viability of cells in Reference Example 4.

FIG. 2 is a graph showing the viability of cells. In FIG. 2, the horizontal axis indicates the type and volume ratio ($V_{CO}:V_{O2}$) of the gas contained in the micro bubbles, and the vertical axis indicates the absorbance. As shown in FIG. 2, the viability of cells was improved in the composition including micro bubbles that contains CO and $O_2$ or a mixed gas thereof as compared to Control. In addition, the viability of cells was significantly improved in the composition having a volume ratio ($V_{CO}:V_{O2}$) of 2:8 to 3:7. From these results, it was found that the composition or the biomaterial preservation composition of the present invention can preserve cells. Further, since the biomaterial preservation composition of the present invention can preserve cells, it was suggested that the biomaterial preservation composition can also preserve a biomaterial composed of cells.

Reference Example 5

It was examined that the biomaterial preservation composition of the present invention can preserve platelets.

(1) Production of Composition

A composition was produced in the same manner as in Reference Example 4(1) except that the volume ratio ($V_{CO}:V_{O2}$) was set to 3:7.

(2) Characteristics of Composition

The physical properties of the composition were measured in the same manner as in Reference Example 4 (2) except that the composition of Reference Example 5(1) was used instead of the composition of Reference Example 4(1) and allowed to stand for about 2 hours. As a result, the mean diameter of the micro bubbles in the composition was 93.6 nm, and the density of the micro bubbles in the composition was $6.87 \times 10^8$ bubbles/ml.

(3) Platelet Preservation

Platelets were prepared from peripheral blood from rabbit ear veins. Specifically, 8 ml of blood was collected from the ear vein of a rabbit at a time, and then 3 ml of anticoagulant solution (10% ACD-A solution, 3.13% sodium citrate) was added to the obtained blood and the blood was shaken gently. The platelets were then separated by performing centrifugation twice on the blood after being shaken. First, centrifugation was performed at 200×g for 10 minutes according to the preparation method for PRP (Platelet Rich Plasma) at 24° C. The centrifugation was then performed again on the obtained PRP at 2000×g for 10 minutes at 24° C. to separate platelet. The composition was added to the obtained platelet of $5 \times 10^6$ platelet/ml to $2 \times 10^7$ platelet/ml to achieve the micro bubble density of $5 \times 10^8$ bubbles/ml. The obtained mixture was preserved at normal temperature (about 25° C.) for 3 days. The number of platelets was also counted at the start of preservation and on day 1, 2, or 3 after preservation. The increase-decrease rate in the number of platelets on day 1, 2, or 3 after preservation was calculated with the number of platelets at the start of preservation being considered as 100% (Example). As Comparative Example, the increase-decrease rate in the number of platelets was calculated in the same manner as described above except that an ACD-A solution was used. The results are shown in FIG. 3.

Figure 3:
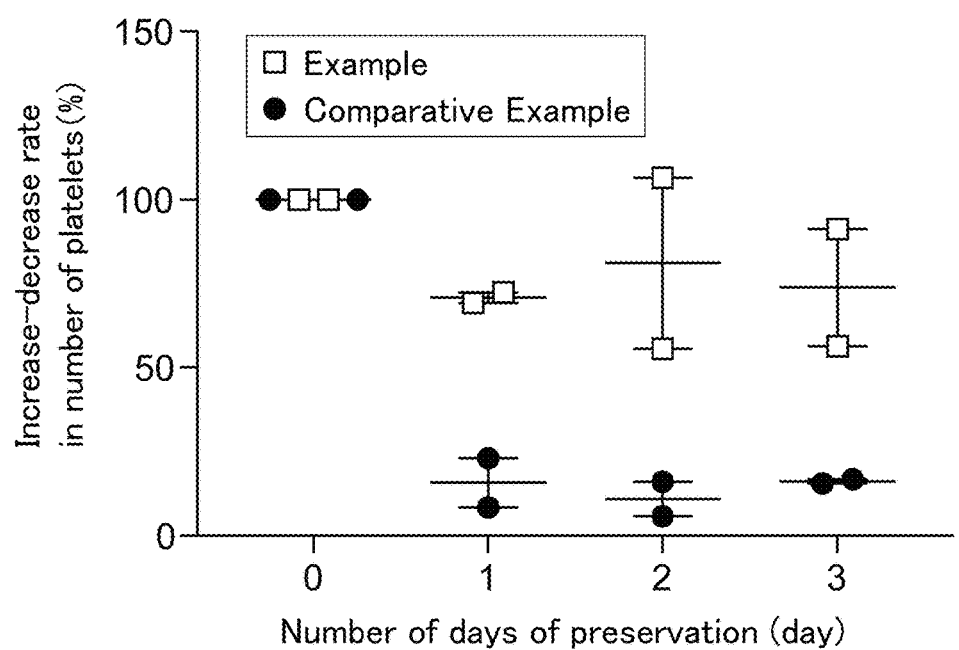
FIG. 3 is a graph showing the increase-decrease rate in the number of platelets in Reference Example 5.

FIG. 3 is a graph showing the increase-decrease rate in the number of platelets. In FIG. 3, the horizontal axis indicates the number of days of preservation, and the vertical axis indicates the increase-decrease rate in the number of platelets. As shown in FIG. 3, the number of platelets was significantly increased on any of the preservation days in Example as compared to Comparative Example and the number of platelets was constant regardless of the number of preservation days in Example. From these results, it was found that the biomaterial preservation composition of the present invention can preserve platelets. Further, since the biomaterial preservation composition of the present invention can preserve cells such as platelets, it was suggested that the biomaterial preservation composition can also preserve a biomaterial composed of cells.

Example 3

It was examined that the biomaterial preservation composition of the present invention can preserve the kidney.

(1) Production of Composition

A composition was produced in the same manner as in Reference Example 4(1) except that the volume ratio ($V_{CO}$:$V_{O2}$) was set to 3:7 and a perfusion preservation solution was used instead of DMEM. As the perfusion preservation solution, Lactec (manufactured by Otsuka Pharmaceutical Co., Ltd.) or University of Wisconsin (UW) solution was used. Hereinafter, the compositions prepared using the Lactec and UW solution are also referred to as a composition L and a composition UW, respectively. Note that, when the compositions were prepared and measured in the same manner as in Reference Example 4 (1) and (2) using a physiological saline which is similar to the perfusion preservation solution, the mean diameter of the micro bubbles in the obtained composition was 131 nm, and the density of the micro bubbles in the obtained composition was $8.04\times10^8$ bubbles/ml. For this reason, it is estimated that the micro bubbles in the composition prepared using the perfusion preservation solution have the same degree of mean diameter and density.

(2) Preparation of Kidney

The kidney was removed from a rat 30 or 40 minutes after death, and blood was removed by introducing the composition L into the blood vessel of the kidney. After the blood removal, the kidney was immersed in the composition UW. In this state, the kidney was preserved at 4° C. for 1 hour or 2 hours. The extracorporeal circulation of the preserved kidney was performed using the composition UW. The renal function was evaluated by measuring the urine volume (integrated value) obtained from the ureter at 10, 20, 30, 40, 50, 60, 70, 80, 90, or 100 minutes after the start of extracorporeal circulation (Example). In addition, in the comparative example, the renal function was evaluated in the same manner except that the perfusion preservation solution was used. The results are shown in FIG. 4.

Figure 4:
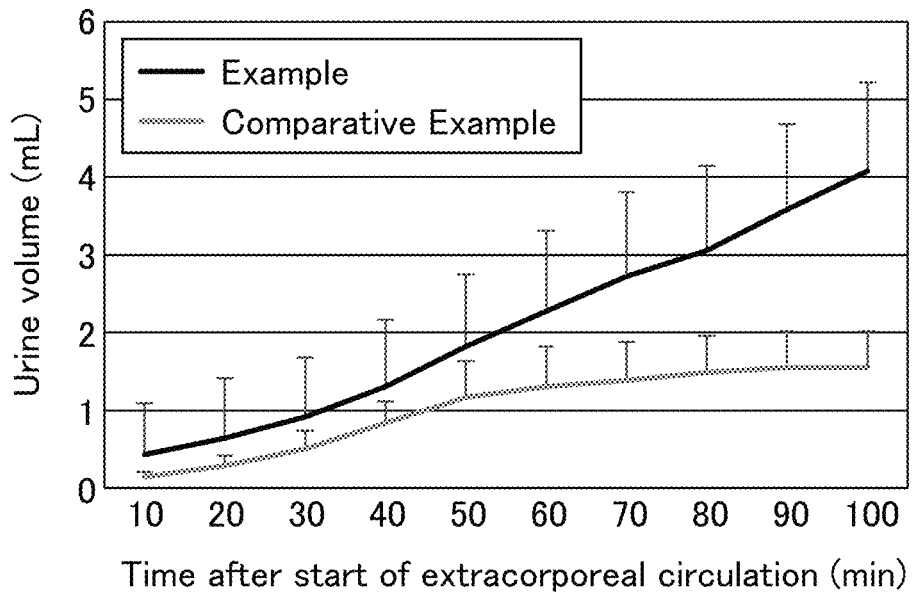
FIG. 4 is a graph showing the urine volume in the kidney after preservation in Example 3.

FIG. 4 is a graph showing the urine volume of kidney after 1 hour of preservation for the kidney 40 minutes after death. In FIG. 4, the horizontal axis indicates time after the start of extracorporeal circulation, and the vertical axis indicates the urine volume. As shown in FIG. 4, the urine volume was increased at any time in Example as compared to Comparative Example. In other words, it was found that the kidney function was maintained in Example as compared to Comparative Example. The difference in urine volume between Example and Comparative Example was particularly remarkable after 50 minutes from the start of extracorporeal circulation. From these results, it was found that the biomaterial preservation composition of the present invention can suppress kidney damage during reperfusion, and thereby restore kidney function after transplantation. The same was true when the kidney 30 minutes after death was preserved at 4° C. for 2 hours. From these results, it was found that the biomaterial preservation composition of the present invention can preserve the kidney, that is, a complex structure such as a laminate of cell sheets.

Reference Example 6

It was examined that the biomaterial preservation composition of the present invention can preserve cells.

(1) Production of Composition

A composition was prepared in the same manner as in Reference Example 4(1) except that hydrogen sulfide (manufactured by Sumitomo Seika Chemicals Co., Ltd.) and medical oxygen were used instead of carbon monoxide and medical oxygen, and the volume ratio ($V_{H2SS}$:$V_{O2}$) was set to 2:8.

(2) Characteristics of Composition

The measurement was performed in the same manner as in Reference Example 4 (2) except that the composition of Reference Example 6 (1) was used instead of the composition of Reference Example 4 (1). As a result, the mean diameter of the micro bubbles in the composition was 115.8 nm, and the density of the micro bubbles in the composition was $8.32\times10^8$ bubbles/ml.

(3) Cell Preservation

The viability of the cells was examined by measuring the absorbance in the same manner as in Reference Example 4 (3) except that the composition of Reference Example 6 (1) was used instead of the composition of Reference Example 4 (1). As a Control, the measurement was performed in the same manner as described above except that 10% FCS-containing DMEM medium was used. The results are shown in FIG. 5.

Figure 5:
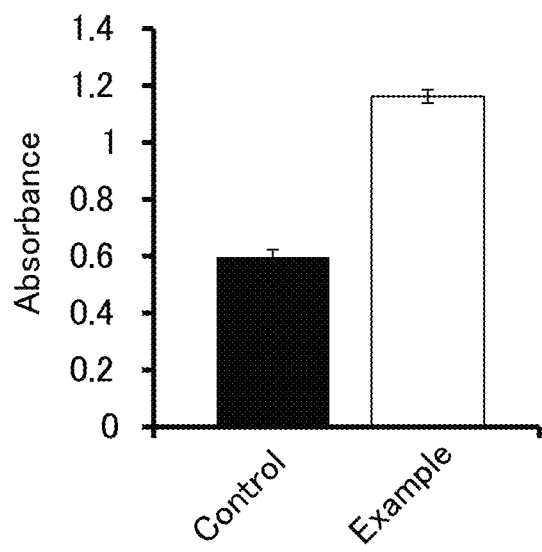
FIG. 5 is a graph showing the viability of cells in Reference Example 6.

FIG. 5 is a graph showing the viability of the cells. In FIG. 5, the horizontal axis indicates the type of sample, and the vertical axis indicates the absorbance. As shown in FIG. 5, the viability of cells was improved in the composition including micro bubbles that contains $H_2S$ as compared to Control. From these results, it was found that the biomaterial preservation composition of the present invention can preserve cells. Further, since the biomaterial preservation composition of the present invention can preserve cells, it was suggested that the biomaterial preservation composition can also preserve a biomaterial composed of cells.

Example 5

It was examined that the biomaterial preservation composition of the present invention can preserve the lung.

(1) Production of Composition

A composition was produced in the same manner as in Reference Example 4 (1) except that the volume ratio ($V_{CO}$:$V_{O2}$) was set to 3:7 and a perfusion preservation solution was used instead of DMEM. As the perfusion preservation solution, Lactec (manufactured by Otsuka Pharmaceutical Co., Ltd.) or University of Wisconsin (UW) solution was used. Hereinafter, the compositions prepared using the Lactec and the UW solution are also referred to as a composition L and a composition UW, respectively. Note that, when the compositions were prepared and measured in the same manner as in Reference Example 4(1) and (2) using a physiological saline which is similar to the perfusion preservation solution, the mean diameter of the micro bubbles in the obtained composition was 131 nm, and the density of the micro bubbles in the obtained composition was $8.04\times10^8$ bubbles/ml. For this reason, it is estimated that the micro bubbles in the composition prepared using the perfusion preservation solution have the same degree of mean diameter and density.

(2) Preparation of Lung

The lung was removed from a living rat or a rat 40 minutes or 2 hours after sacrifice with potassium chloride, and blood was removed by introducing the composition L into the blood vessel of the lung. After the blood removal, the lung was immersed in the composition UW. In this state, the lung was preserved at 4° C. for 24 hours. After the preservation, it was evaluated whether organs were preserved by measuring the weight of the lung. As Control 1, the evaluation was made in the same manner except that the lung was not preserved after removal. As Control 2, the evaluation was made in the same manner except that the Lactec and the UW solution were used instead of the composition L and the composition UW. The results are shown in FIG. 6.

Figure 6:
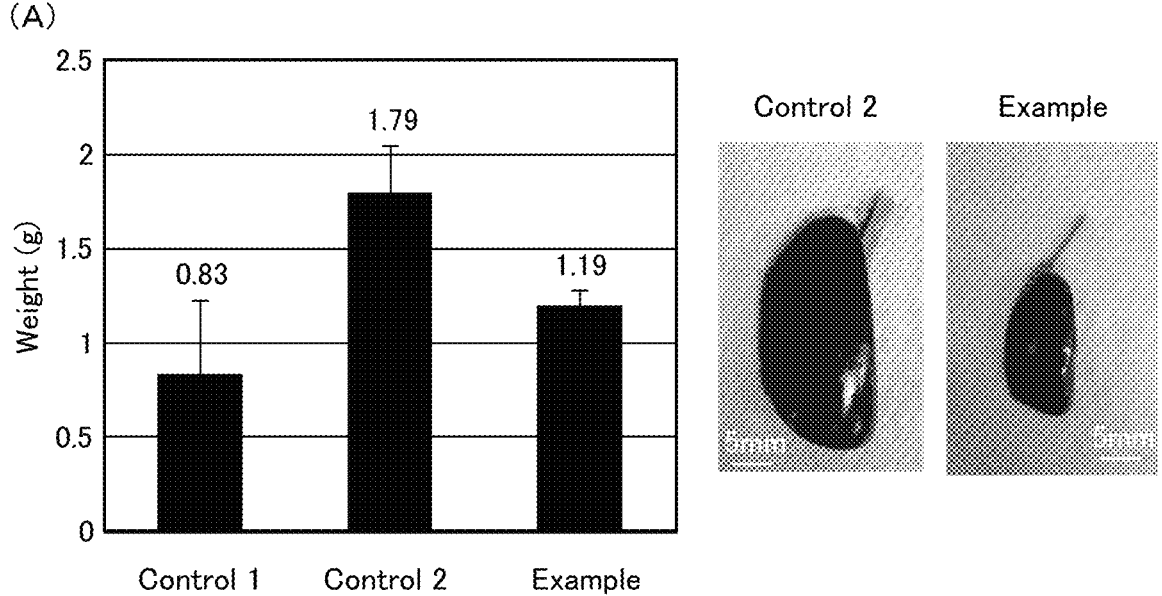
FIG. 6 (A) and (B) are graphs showing the weight of the lung after preservation in Example 5.
Figure 6:
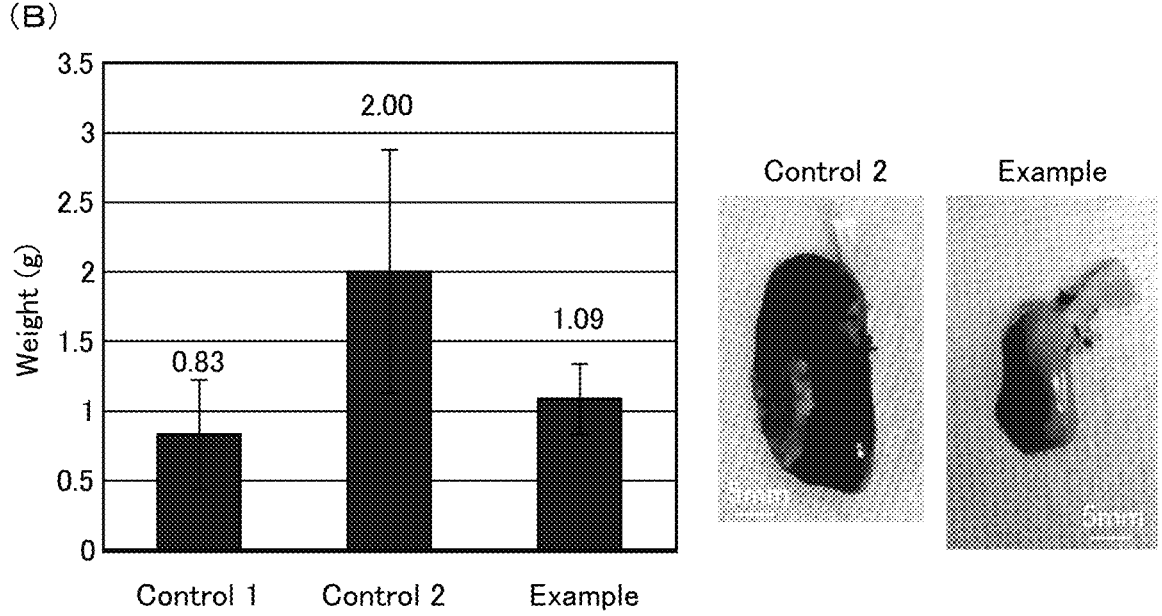

FIG. 6 shows graphs each showing the weight of the lung after preservation. In FIG. 6, (A) shows the results of the lung removed from a living rat, and (B) shows the results of the lung from a rat 2 hours after sacrifice. In each of the graphs of FIG. 6, the horizontal axis indicates the type of sample, and the vertical axis indicates the weight of the lung. As shown in FIG. 6, the weight of the lung was increased in Control 2, whereas the increase of the weight of the lung was suppressed in Example, which was about the same as in Control 1. From these results, it was found that, the composition or the cell preservation composition of the present invention can suppress an increase in weight of a lung during preservation, i.e., can prevent an edema of a lung. The same was true when the lung derived from a rat 40 minutes after sacrifice was used. From these results, it was found that the biomaterial preservation composition of the present invention can preserve the lung, that is, a complex structure such as a laminate of cell sheets.

Reference Example 7

Figure 7:
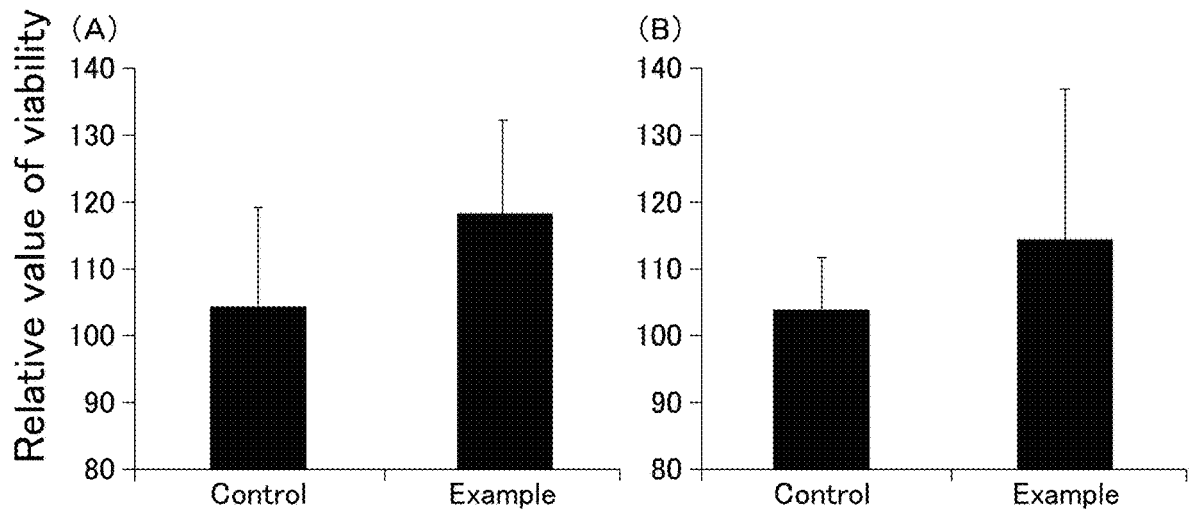
FIG. 7 (A) and (B) are graphs showing the viability of cells in Reference Example 7.

It was examined that the biomaterial preservation composition of the present invention can preserve cells.
(1) Production of Composition
A composition was produced in the same manner as in Reference Example 4 (1) except that air (manufactured by Sumitomo Seika Chemicals Co., Ltd.) was used instead of carbon monoxide and medical oxygen, and a HUVEC medium was used instead of the DMEM medium. As the HUVEC medium, an EGM2 (Endothelial Cell Basal Medium 2) medium was used.
(2) Characteristics of Composition
The measurement was performed in the same manner as in Reference Example 4 (2) except that the composition of Reference Example 7 (1) was used instead of the composition of Reference Example 4 (1). As a result, the mean diameter of the micro bubbles in the composition was 126.2 nm, and the density of the micro bubbles in the composition was $6.84 \times 10^8$ bubbles/ml.
(3) Cell Preservation
Human vascular endothelial cells (HUVEC cells, obtained from Promo Cell) were suspended in the composition, and the obtained cell suspension was seeded in a 96-well dish so as to achieve 80% confluent/well. Then, the resultant was cultured under the following condition 1 or 2. After the culture, the viability of cells was examined by measuring the absorbance of each well using the MTT assay kit based on the attached protocol. As a control, the viability of cells was examined in the same manner except that the HUVEC medium was used. The relative value of the viability was calculated with the viability of the control being considered as 100%. The results are shown in FIG. 7.
Condition 1:
Culture in the presence of a composition (micro bubble density: $6.84 \times 10^8$ bubbles/ml) at 0.5 to 1% $O_2$ and 37° C. for 48 hours, followed by culture in the presence of the composition (micro bubble density: $6.84 \times 10^8$ bubbles/ml) at 4° C. for 24 hours.

Condition 2:
Culture in the presence of a HUVEC medium for 48 hours at 0.5 to 1% $O_2$ and 37° C., followed by culture in the presence of the composition (micro bubble density: $6.84 \times 10^8$ bubbles/ml) at 4° C. for 24 hours.

FIG. 7 shows graphs each showing the viability of cells. In FIG. 7, (A) shows the result of Condition 1 and (B) shows the result of Condition 2. In each of the graphs of FIG. 7, the horizontal axis indicates the type of sample, the vertical axis indicates the relative value of the viability. As shown in FIG. 7, in both conditions, when the preservation (culture) was performed in the presence of a composition including micro bubbles, the viability of cells was improved as compared to the case where the preservation (culture) was performed in the presence of a control. From these results, it was found that the biomaterial preservation composition of the present invention can preserve cells. Further, since the biomaterial preservation composition of the present invention can preserve cells, it was suggested that the biomaterial preservation composition can also preserve a biomaterial composed of cells.

Reference Example 8

Figure 8:
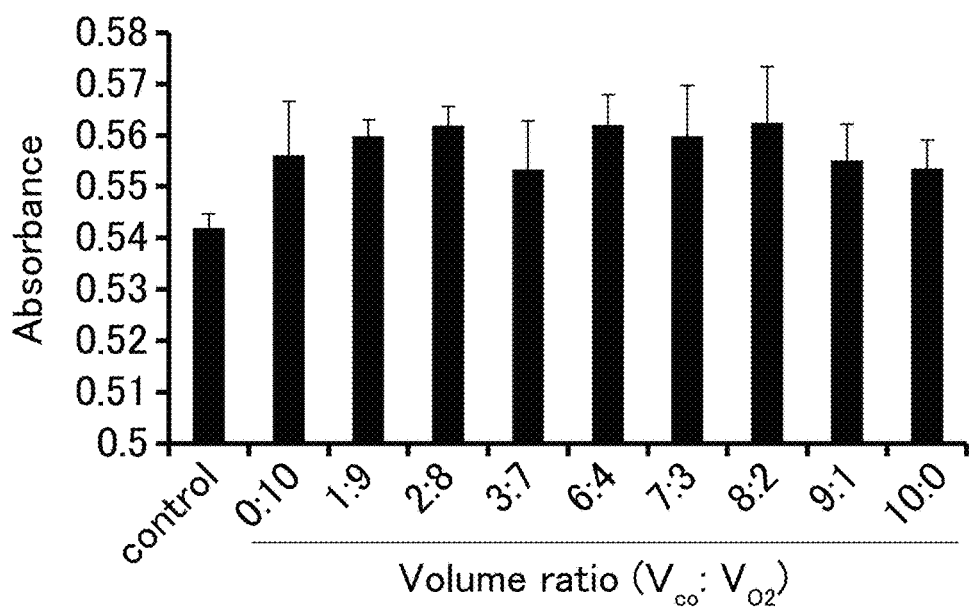
FIG. 8 is a graph showing the viability of cells in Reference Example 8.
Figure 9:
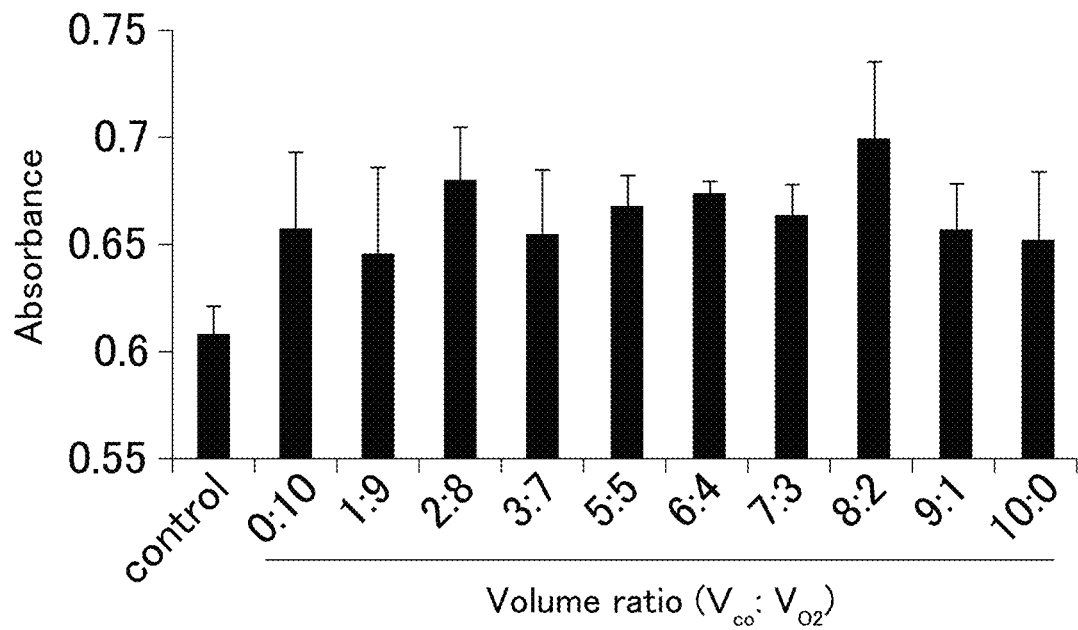
FIG. 9 is a graph showing the viability of cells in Reference Example 8.

It was examined that the composition or the cell preservation composition of the present invention can preserve cells and the cell culture composition of the present invention can suppress the decrease in viability of cells during cell culture.
(1) Production of Composition
The compositions of different volume ratios ($V_{CO}:V_{O2}$) of 0:10, 1:9, 2:8, 3:7, 6:4, 7:3, 8:2, 9:1, and 10:0 were prepared in the same manner as in Reference Example 4 (1) except that the HUVEC medium was used instead of the DMEM medium.
(2) Characteristics of Composition
The measurement was performed in the same manner as in Reference Example 4 (2) except that the composition of Reference Example 8 (1) was used instead of the composition of Reference Example 4 (1). As a result, the mean diameter of the micro bubbles in the composition was 132.3 nm, and the density of the micro bubbles in the composition was $8.89 \times 10^8$ bubbles/ml.
(3) Cell Preservation
Human vascular endothelial cells were suspended in the HUVEC medium, and the obtained cell suspension was seeded in a 96-well dish. Then, after the culture until confluence, the resultant was further cultured under the following condition 3 or 4. After the culture, for each cell, the absorbance of each well was measured using the MTT assay kit based on the attached protocol. As a control, the viability of cells was measured in the same manner except that the composition was not added. The results are shown in FIGS. 8 and 9.
Condition 3:
Culture in the presence of a composition (micro bubble density: $8.89 \times 10^8$ bubbles/ml) at 5% $CO_2$ and 37° C. for 5 days (120 hours), followed by culture in the presence of a HUVEC medium at 5% $CO_2$ and 37° C. for 1 hour.
Condition 4:
Culture in the presence of a HUVEC medium at 0.5 to 1% $O_2$ and 37° C. for 18 hours, followed by culture in the presence of a composition (micro bubble density: $8.89 \times 10^8$ bubbles/ml) at 5% $CO_2$ and 37° C. for 48 hours and culture in the presence of the HUVEC medium at 5% $CO_2$ and 37° C. for 1 hour.

FIG. 8 is a graph showing the viability of cells under Condition 3. In FIG. 8, the horizontal axis indicates the type and volume ratio ($V_{CO}:V_{O2}$) of the gas contained in the micro bubbles, and the vertical axis indicates the absorbance. As shown in FIG. 8, the viability of cells was improved in the composition including micro bubbles that contains CO and $O_2$ or a mixed gas thereof as compared to Control.

Next, FIG. 9 is a graph showing the viability of cells under Condition 4. In FIG. 9, the horizontal axis indicates the type and volume ratio ($V_{CO}:V_{O2}$) of the gas contained in the micro bubbles, and the vertical axis indicates the absorbance. As shown in FIG. 9, the viability of cells was improved in the composition including micro bubbles that contains CO and $O_2$ or a mixed gas thereof as compared to Control.

From these results, it was found that the biomaterial preservation composition of the present invention can preserve cells. Further, since the biomaterial preservation composition of the present invention can preserve cells, it was suggested that the biomaterial preservation composition can also preserve a biomaterial composed of cells.

Reference Example 9

It was examined that the biomaterial preservation composition having a different bubble density can preserve cells.

(1) Production of Composition

A composition (composition ($CO/O_2$)) having a volume ratio ($V_{CO}:V_{O2}$) of 3:7 was produced in the same manner as in Reference Example 4 (1) except that a HUVEC medium was used instead of the DMEM medium. In addition, a composition (composition (Air)) was produced in the same manner as in Reference Example 4 (1) except that the air was used instead of carbon monoxide and medical oxygen, and a HUVEC medium was used instead of the DMEM medium. In addition, a composition (composition ($H_2S/O_2$)) was produced in the same manner as in Reference Example 4 (1) except that hydrogen sulfide and medical oxygen were used instead of carbon monoxide and medical oxygen, the volume ratio ($V_{H2S}:V_{O2}$) was set to 2:8, and a HUVEC medium was used instead of the DMEM medium.

(2) Characteristics of Composition

The measurement was performed in the same manner as in Reference Example 4 (2) except that the composition of Reference Example 9 (1) was used instead of the composition of Reference Example 4 (1). As a result, the mean diameter of the micro bubbles and the density of the micro bubbles in each composition were as follows.

Composition ($CO/O_2$) mean diameter: 132.3 nm, density: $8.89 \times 10^8$ bubbles/ml Composition (Air) mean diameter: 126.2 nm, density: $6.84 \times 10^8$ bubbles/ml Composition ($H_2S/O_2$) mean diameter: 115.8 nm, density: $8.32 \times 10^8$ bubbles/ml (3) Cell Preservation A cell suspension of the rat cardiac rhabdomyocytes (H9c2 cells) or the human vascular endothelial cells (HUVEC cells) was seeded in a 96-well dish so as to achieve 80% confluent/well. Then, the resultant was cultured under the following conditions 5 to 9. The composition-added medium of each condition was obtained by adding the composition so that each composition was diluted to a predetermined concentration (1 fold (undiluted), ½ fold, ⅕ fold, 1/10 fold, 1/50 fold, 1/100 fold, or 1/1000 fold). After the culture, the viability of cells was examined by measuring the absorbance of each well using the MTT assay kit based on the attached protocol. As a control, the viability of cells was examined in the same manner except that the composition was not added. The relative value of the viability was calculated with the viability of the control being considered as 100%. The results are shown in FIGS. 10 to 14.

Condition 5 (H9c2 Cells):
Culture in the presence of a composition-non-added medium at 0.5 to 1% $O_2$ and 37° C. for 24 hours, followed by culture in the presence of a composition-added medium (Air) at 4° C. for 6 hours.

Condition 6 (H9c2 Cells):
Culture in the presence of a composition-added medium (Air) at 0.5 to 1% $O_2$ and 37° C. for 24 hours, followed by culture in the presence of a composition-added medium (Air) at 4° C. for 6 hours.

Condition 7 (H9c2 Cells):
Culture in the presence of a composition-non-added medium at 0.5 to 1% $O_2$ and 37° C. for 24 hours, followed by culture in the presence of a composition-added medium ($CO/O_2$) at 5% $CO_2$ and 4° C. for 6 hours.

Condition 8 (HUVEC Cells):
Culture in the presence of a composition-non-added medium at 0.5 to 1% $O_2$ and 37° C. for 24 hours, followed by culture in the presence of a composition-added medium (Air) at 4° C. for 6 hours.

Condition 9 (HUVEC Cells):
Culture in the presence of a composition-non-added medium at 0.5 to 1% $O_2$ and 37° C. for 48 hours, followed by culture in the presence of a composition-added medium ($H_2S/O_2$) at 4° C. for 24 hours.

Figure 10:
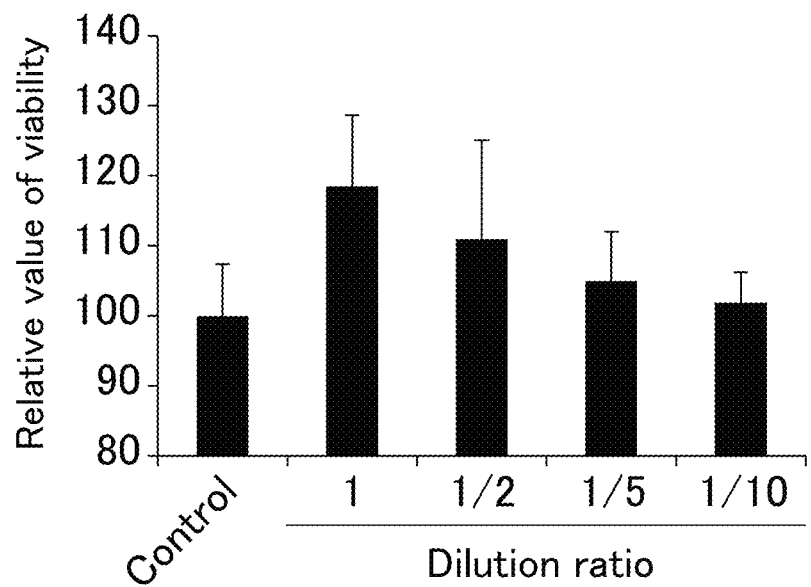
FIG. 10 is a graph showing the relative values of viability of cells in Reference Example 9.

FIG. 10 is a graph showing the viability of cells under Condition 5. In FIG. 10, the horizontal axis indicates the dilution series of the composition, and the vertical axis indicates the relative value of viability. As shown in FIG. 10, the viability of cells was improved depending on the composition concentration (the micro bubble density) as compared to Control.

Figure 11:
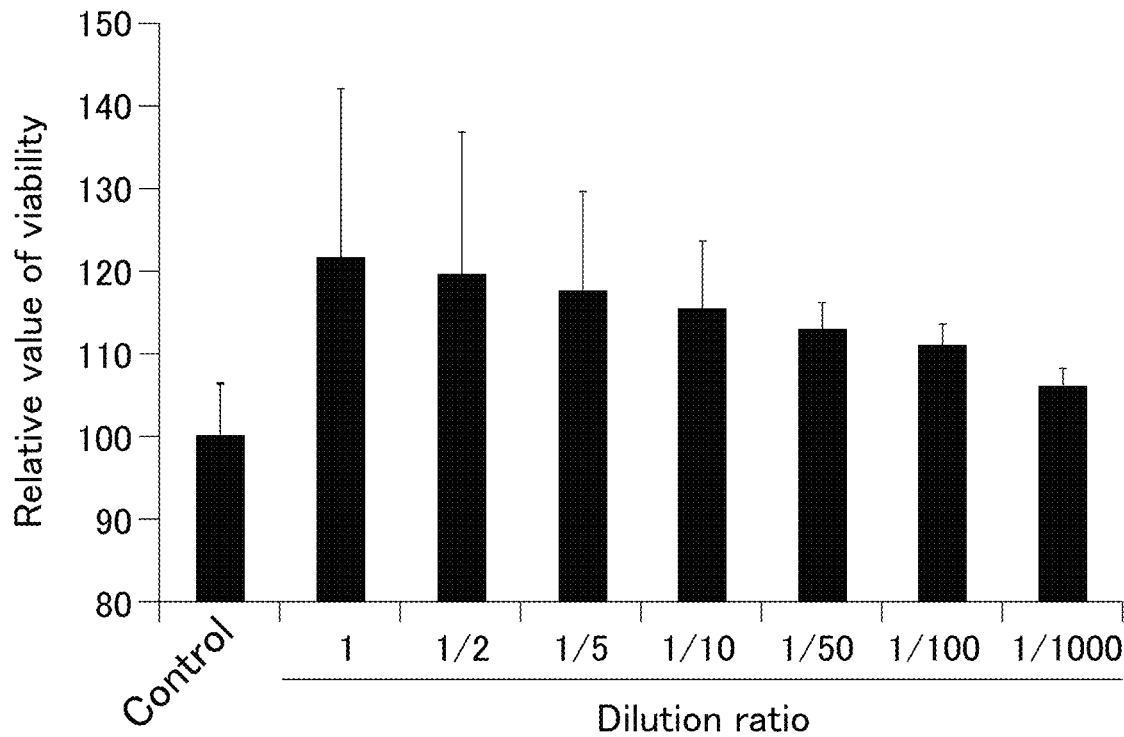
FIG. 11 is a graph showing the relative values of viability of cells in Reference Example 9.

FIG. 11 is a graph showing the viability of cells under Condition 6. In FIG. 11, the horizontal axis indicates the dilution series of the composition, and the vertical axis indicates the relative value of viability. As shown in FIG. 11, the viability of cells was improved depending on the composition concentration (the micro bubble density) as compared to Control.

Figure 12:
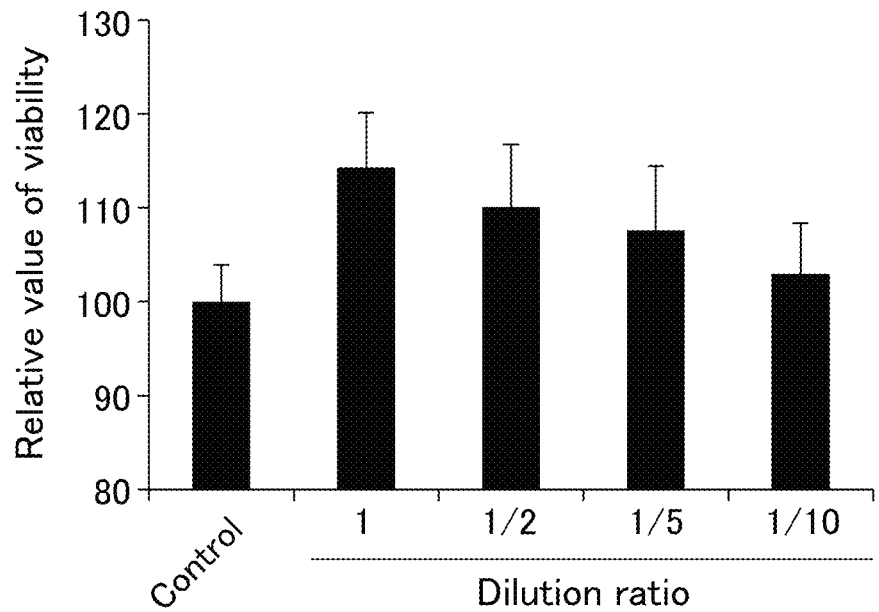
FIG. 12 is a graph showing the relative values of viability of cells in Reference Example 9.

FIG. 12 is a graph showing the viability of cells under Condition 7. In FIG. 12, the horizontal axis indicates the dilution series of the composition, and the vertical axis indicates the relative value of viability. As shown in FIG. 12, the viability of cells was improved depending on the composition concentration (the micro bubble density) as compared to Control.

Figure 13:
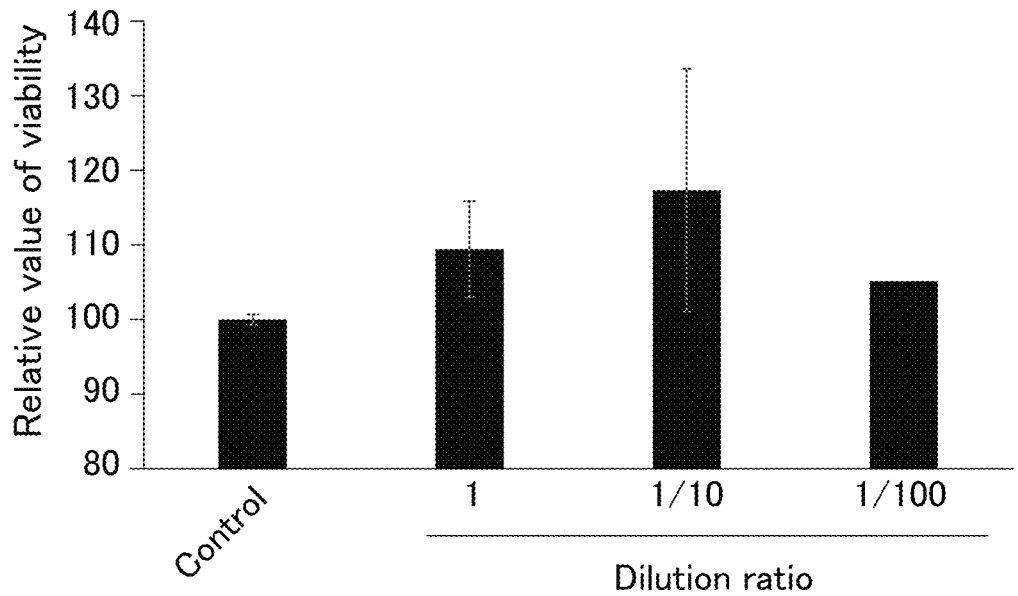
FIG. 13 is a graph showing the relative values of viability of cells in Reference Example 9.

FIG. 13 is a graph showing the viability of cells under Condition 8. In FIG. 13, the horizontal axis indicates the dilution series of the composition, and the vertical axis indicates the relative value of viability. As shown in FIG. 13, the viability of the cells was improved depending on the composition concentration (micro bubble density) as compared to Control.

Figure 14:
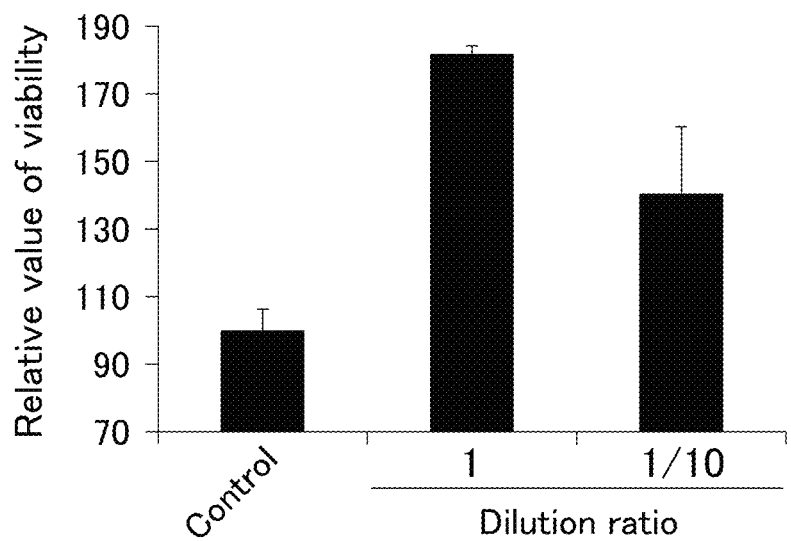
FIG. 14 is a graph showing the relative values of viability of cells in Reference Example 9.

FIG. 14 is a graph showing the viability of cells under Condition 9. In FIG. 14, the horizontal axis indicates the dilution series of the composition, and the vertical axis indicates the relative value of viability. As shown in FIG. 14, the viability of cells was improved depending on the composition concentration (micro bubble density) as compared to Control.

From the above, it was found that the biomaterial preservation composition having a different bubble density can preserve cells and the biomaterial preservation composition having a different bubble density can suppress the decrease in viability of cells during cell culture. In addition, since the cell preservation effect was enhanced depending on the micro bubble density regardless of the type of gas contained in the micro bubbles, it was found that the micro bubbles have a cell preservation effect and a biomaterial preservation effect. Further, from the micro bubble content of each composition, it was found that the cell preservation effect and the biomaterial preservation effect were further enhanced by setting the micro bubble density to $5 \times 10^5$ bubbles/ml or more, preferably $1 \times 10^6$ bubbles/ml or more, more preferably to $5 \times 10^6$ bubbles/ml or more, or $1 \times 10^7$ bubbles/ml or more. Further, as shown in Reference Example 1 described below, there is substantially no dissolved gas in the composition used in Reference Example 9. Further, as shown in Reference Example 2 described below, micro bubbles are also present in the composition after being stand. Therefore, it was estimated that the micro bubble density in the solvent associates with the cell preservation effect and the biomaterial preservation effect.

Example 9

It was examined that the biomaterial preservation composition of the present invention can preserve the heart.

(1) Production of Composition

A composition was produced in the same manner as in Reference Example 4 (1) except that the volume ratio ($V_{CO}:V_{O2}$) was set to 3:7 and an ET-Kyoto solution (ETK, manufactured by Otsuka Pharmaceutical Co., Ltd.) was used instead of the distilled water.

(2) Characteristics of Composition

When the composition was prepared using physiological saline which is similar to the ETK, the mean diameter of micro bubbles in the obtained composition was 131 nm and the micro bubble density was $8.04 \times 10^8$ bubbles/ml. For this reason, it is estimated that the micro bubbles in the composition prepared using the ETK have the same degree of mean diameter and density.

(3) Preparation of Heart

Six-week-old LEW/SsN Slc male rats (n=5) were given pentobarbital (manufactured by Kyoritsu Pharmaceutical) at a dose of 50 mg/kg (drug/body weight) and deeply anesthetized. The hearts were then removed from the rats. Further, after dissection of the aorta and pulmonary artery of the heart, the composition was injected to remove blood to prepare heart.

(4) Heart Preservation

The heart preservation was performed using the preservation device of JP 2015-174823A. Specifically, a flask containing distilled water was placed in the preservation device shown in FIG. 2 of JP 2015-174823A. Further, a biomaterial suspending unit was placed in the flask, and the heart was suspended in the biomaterial suspending unit. Carbon monoxide and oxygen were supplied by the medical-gas supplying unit so that the partial pressure of carbon monoxide ($PCO$) and the partial pressure of oxygen ($PO_2$) in the preservation chamber became 0.15 MPa and 0.2 MPa, respectively. Then, in this state, the heart was preserved in a refrigerator at 4° C. for 48 hours.

After the preservation, the heart was transplanted into a rat to examine the size and beating of heart. As Control 1, the transplantation and examination were performed in the same manner except that perfusion was performed using ETK containing no micro bubble instead of the composition. As Control 2, the transplantation and examination were performed in the same manner except that perfusion was performed using ETK in which CO and $O_2$ were dissolved instead of the composition. The ETK in which CO and $O_2$ were dissolved was prepared by introducing CO, $O_2$, and EKT into a sealed container, sealing the container, and inverting and mixing for 10 minutes. The results are shown in FIG. 15.

Figure 15:
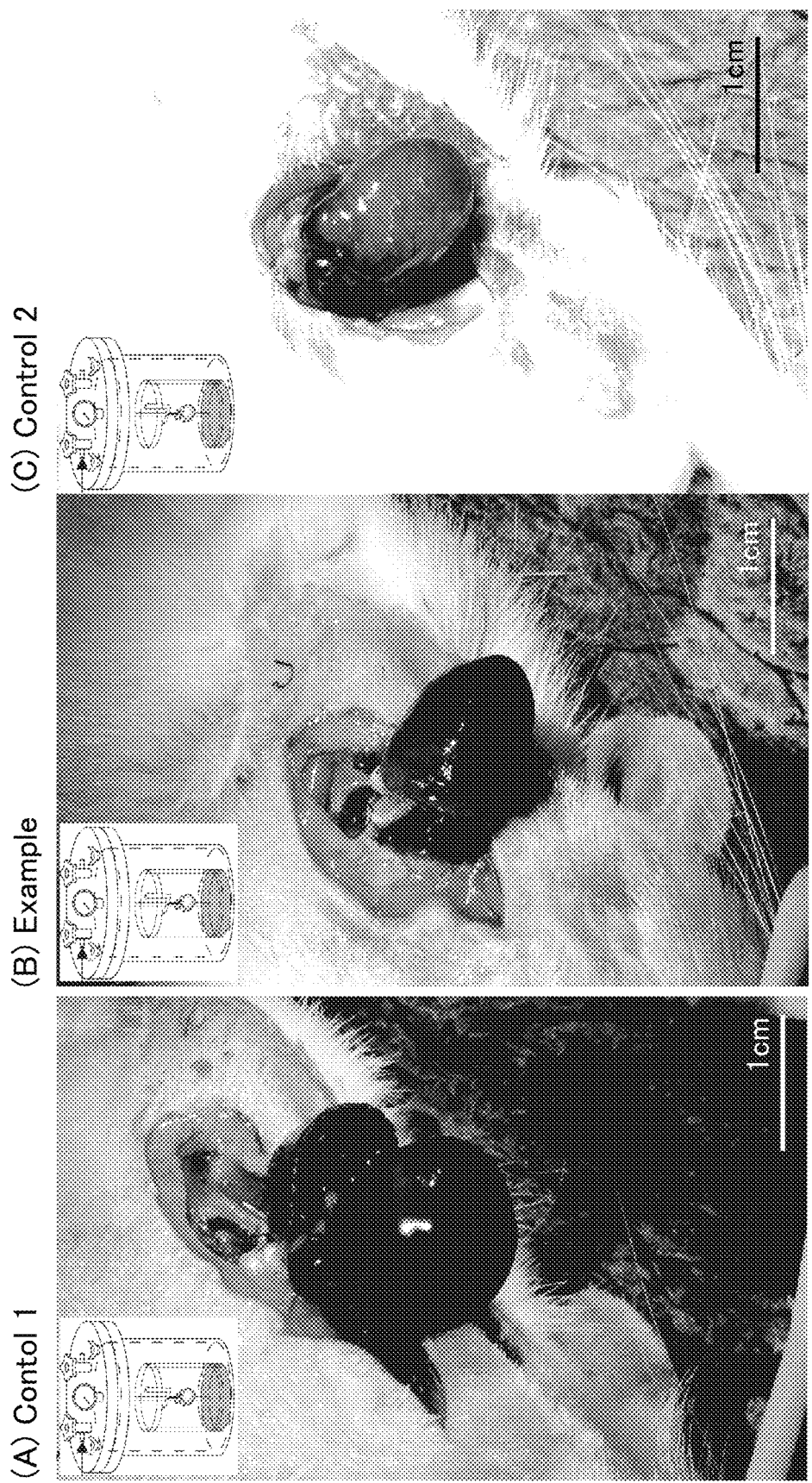
FIG. 15 (A) to (C) show photographs each showing the heart after transplantation in Example 9.

FIG. 15 shows photographs each showing the heart after transplantation. The drawing shown in the upper left of each photograph of FIG. 15 is a schematic diagram showing the preservation state in the preservation device. In FIG. 15, (A) shows the result of Control 1, (B) shows the result of using the composition, and (C) shows the result of Control 2. As shown in FIG. 15, when the heart was perfused and preserved using the composition, swelling or edema due to congestion of the heart was suppressed as compared to Controls 1 and 2 and the size of the heart before the preservation was maintained. In Control 1, the beating of heart could not be confirmed, and in Control 2, the beating of heart could hardly be confirmed. On the other hand, when the heart was perfused and preserved using the composition, the beating of heart could be confirmed. From these results, it was found that the biomaterial preservation composition of the present invention can preserve the heart.

Example 10

It was examined that compositions including micro bubbles of similar density can be produced regardless of the type of gas.

(1) Production of Composition

A composition including micro bubbles that contains oxygen, carbon monoxide, a mixed gas of oxygen and carbon monoxide, carbon dioxide, or nitrogen as a gas was produced in the same manner as Reference Example 4 (1) except that carbon dioxide (manufactured by Sumitomo Seika Chemicals Co., Ltd.) and nitrogen (manufactured by Sumitomo Seika Chemicals Co., Ltd.) were used in addition to carbon monoxide and medical oxygen and physiological saline was used instead of the DMEM medium. All the producing conditions except for the gas were the same.

(2) Characteristics of Composition

The measurement was performed in the same manner as in Reference Example 4 (2) except that the composition of Example 10(1) was used instead of the composition of Reference Example 4 (1). Note that, for each composition, the same measurement was performed three times. As a result, the mean diameters of the micro bubbles containing each gas in the composition were as follows. The micro bubble densities of the respective gases are shown in FIG. 16.

Figure 16:
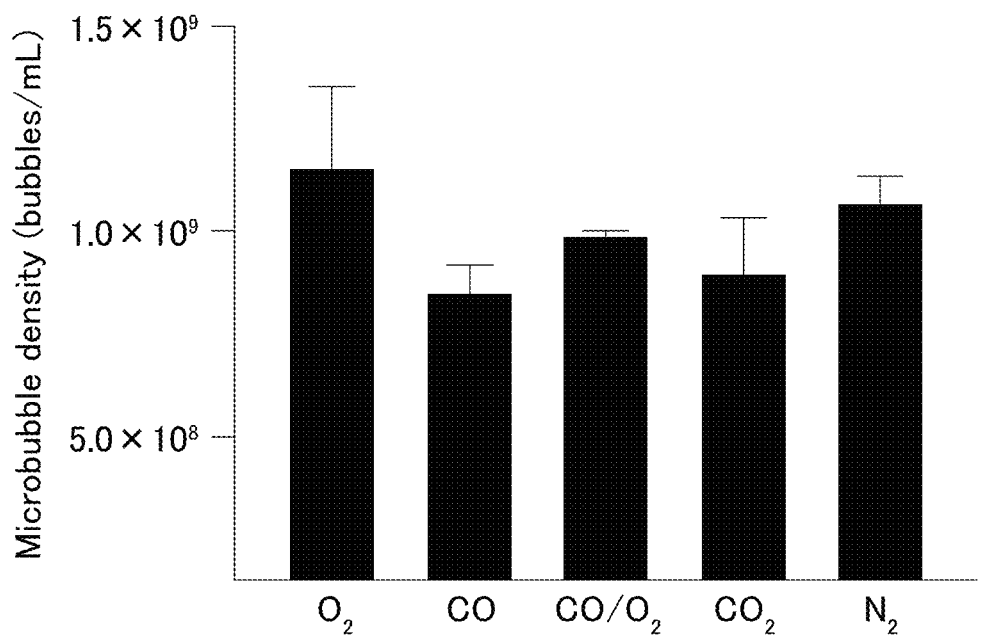
FIG. 16 is a graph showing the density of micro bubbles containing each gas in Example 10.

Composition ($O_2$) mean diameter: 104.5 nm
Composition (CO) mean diameter: 117.0 nm
Composition (CO/$O_2$) mean diameter: 112.3 nm
Composition ($CO_2$) mean diameter: 117.5 nm
Composition ($N_2$) mean diameter: 132.7 nm FIG. 16 is a graph showing the densities of micro bubbles containing the respective gases. In FIG. 16, the horizontal axis indicates the type of gas contained in the micro bubbles, and the vertical axis indicates the micro bubble density. As shown in FIG. 16, when the composition was produced under the same condition, the micro bubble density was about $1 \times 10^9$ bubbles/ml regardless of the type of gas introduced into the micro bubbles. From these results, it was found that compositions including micro bubbles of similar density can be produced regardless of the type of gas.

Example 11

It was examined that the biomaterial can be preserved by pretreating the biomaterial with the biomaterial preservation composition of the present invention.

(1) Production of Composition

A composition of different volume ratio ($V_{CO}$:$V_{O2}$)=10:0 was produced in the same manner as in Reference Example 4 (1) except that the physiological saline was used instead of the DMEM medium.

(2) Characteristics of Composition

The measurement was performed in the same manner as in Reference Example 4 (2) except that the composition of Example 11 (1) was used instead of the composition of Reference Example 4 (1). As a result, the mean diameter of the micro bubbles in the composition was about 100 nm, and the density of the micro bubbles in the composition was about $1\times10^9$ bubbles/ml.

(3) Pretreatment of Heart

Six-week-old LEW/SsN Slc male rats (n=6) were given pentobarbital (manufactured by Kyoritsu Pharmaceutical) at a dose of 50 mg/kg (drug/body weight) and deeply anesthetized. The hearts were then removed from the rats. Further, the aorta and pulmonary artery of the heart were dissected and removed.

(4) Preservation of Heart

The composition was injected to the obtained heart to remove blood, thereby pretreating heart. After the pretreatment, the heart was perfused by injecting the UW solution. Then, the heart was immersed in the UW solution and preserved in a refrigerator at 4° C. for 24 hours.

After the preservation, the heart was transplanted into a rat to check the beating of heart. The beating of heart was evaluated based on whether both the ventricles and the atria were beating or only the ventricles were beating. Specifically, if both the ventricles and atria of the heart were beating, it was evaluated that the function of the heart was maintained, and if only the ventricles of the heart were beating, it was evaluated that the function of the heart was not maintained. As a Control, the transplantation and examination were performed in the same manner except that perfusion was performed using physiological saline containing no micro bubble instead of the composition. The results are shown in FIG. 17.

Example 12

It was examined that the micro bubble density in the solvent can be improved by producing micro bubbles in the presence of a surfactant.

Figure 17:
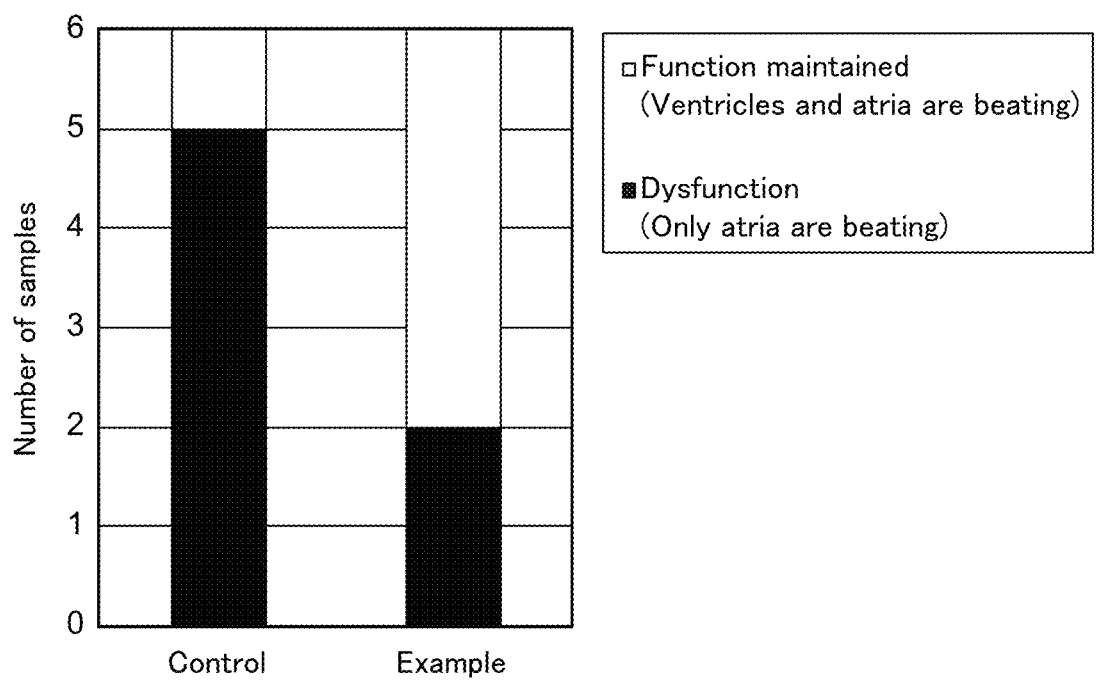
FIG. 17 is a graph showing the evaluation result of the heart after preservation in Example 11.

FIG. 17 is a graph showing the evaluation results of the heart after preservation. In FIG. 17, the horizontal axis indicates the type of sample, and the vertical axis indicates the number of samples. As shown in FIG. 17, the function of the heart of Example pretreated with the composition of the present invention was maintained in 4 out of 6 cases, whereas the function of the heart of Control was maintained in only 1 out of 6 cases after preservation. Although it is not shown, the heart of Example was bright red, suggesting that the blood circulation in the heart was good, whereas the heart of Control was dark brown, suggesting that the blood circulation in the heart was poor, and reduced hemoglobin was retained between the myocardium. From these results, it was found that the biomaterial can be preserved by pretreating the biomaterial with the biomaterial preservation composition of the present invention.

Figure 18:
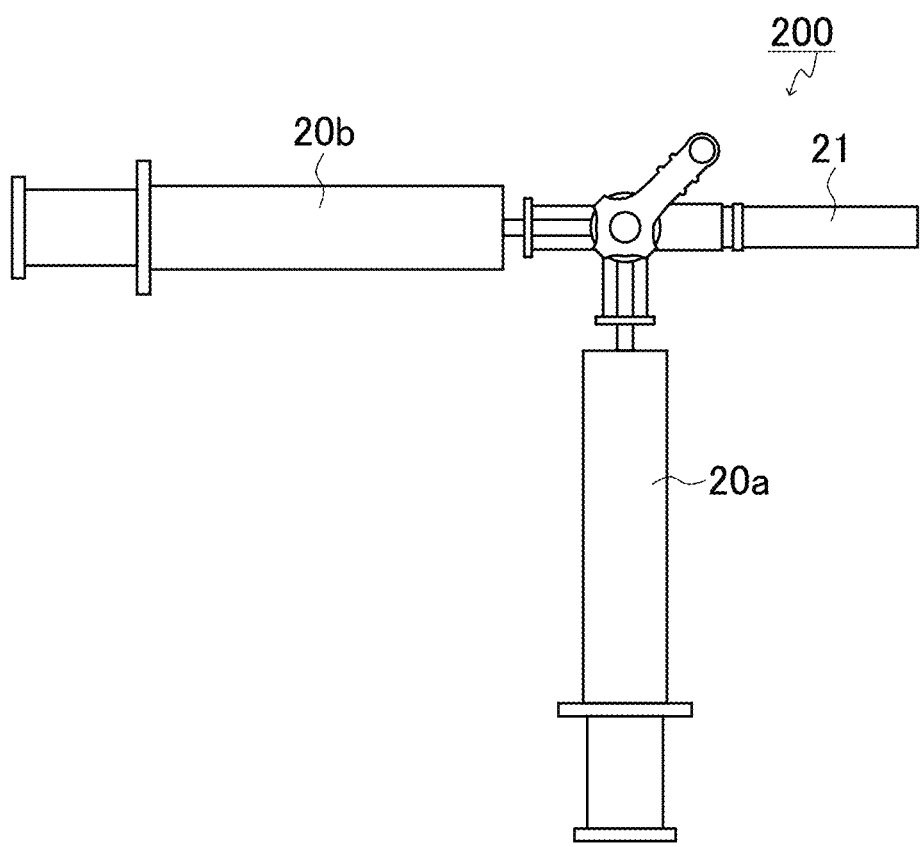
FIG. 18 is a schematic diagram showing an apparatus for producing micro bubbles in Example 12.

A composition of the present invention was produced using distilled water in which a cationic surfactant, dimethydioctadecylammonium chromido (FUJIFILM Wako Pure Chemical Corporation), was added so as to achieve the concentration of 10 mmol/l, and a production apparatus 200 of FIG. 18. As shown in FIG. 18, the production apparatus 200 includes two syringes 20a and 20b (10 ml-syringes) and a venturi-type three-way stopcock 21 (a three-way stopcock with a constriction). The two syringes 20a and 20b are fitted at their distal ends with the three-way stopcock 21. First, the syringes 20a and 20b were released from the three-way stopcock 21. Next, 5 ml of distilled water containing the cationic surfactant was introduced into the interior of the syringe 20a so that no air was contained in the syringe 20a, and the syringe 20a was again fitted with the three-way stopcock 21. After the fitting, distilled water in the syringe 20a was introduced into the three-way stopcock 21 and extruded to a fitting port of the syringe 20b of the three-way stopcock 21. On the other hand, about 5 ml of air was introduced into the syringe 20b so as to correspond to 5 ml of distilled water introduced into the syringe 20a, and the syringe 20b was again fitted with the three-way stopcock 21. Thereafter, the piston was shuttled ten times (approximately 2 seconds/1 reciprocations) in the syringes 20a and 20b, and the syringes 20a and 20b were then sonicated (60 W) for 5 to 10 seconds. A composition (Examples 12-1) was produced by further carrying out the same treatment two more times. A composition (Example 12-2) was produced in the same manner except that the cationic surfactant was not added. Compositions (SDS: Example 12-3, Triton X-100: Example 12-4) were produced in the same manner except that, instead of the dimethyldioctadecylammonium chloride, sodium lauryl sulfate (SDS, manufactured by Wako Pure Chemical Industries, Ltd.) as an anionic surfactant was added so as to achieve 100 mmol/l or octylphenol ethoxylate (Triton X-100, manufactured by Wako Pure Chemical Industries, Ltd.) as a nonionic surfactant was added so as to achieve 10 mmol/l. Then, the physical properties of each of the obtained compositions were measured in the same manner as in Reference Example 4 (2). The measurement was performed at 25° C. As a result, the mean diameter of the micro bubbles in the composition of Example 12-1 was 222.1 nm and the density of the micro bubbles in the composition of Example 12-1 was $1.79\times10^{12}$ bubbles/ml. The mean diameter of the micro bubbles in the composition of Example 12-2 was 109.8 nm and the density of the micro bubbles in the composition of Example 12-2 was $1.30\times10^{10}$ bubbles/ml. The mean diameter of the micro bubbles in the composition of Example 12-3 was 92.5 nm and the density of the micro bubbles in the composition of Example 12-3 was $1.01\times10^{10}$ bubbles/ml. The mean diameter of the micro bubbles in the composition of Example 12-4 was 111.8 nm, and the density of the micro bubbles in the composition of Example 12-4 was $5.78\times10^9$ bubbles/ml. From these results, it was found that the micro bubble density in the solvent can be improved by producing micro bubbles in the presence of a surfactant, particularly a cationic surfactant.

Reference Example 1

It was examined that there was substantially no gas that did not form micro bubbles in the compositions of Examples 3, 5, 9 to 12 and Reference Example 4 to 9. A composition used in Reference Example 1 was produced using a venturi-type micro bubble production apparatus 100 shown in FIG.

1. First, 40 ml of ultrapure water (Milli-Q water) was introduced into the apparatus 100 of FIG. 1, and then the apparatus 100 was shaken to remove bubbles in the apparatus 100 to the outside of the apparatus 100. Next, 5 ml of carbon monoxide was collected in a syringe and then connected to a three-way stopcock 5. After a motor 1 was started to be driven, the three-way stopcock 5 was opened, and carbon monoxide was introduced into the apparatus 100. In this state, the motor 1 was driven for 5, 10, or 30 minutes to produce a composition. After the driving of the motor 1 was stopped, the obtained composition was recovered in a beaker. The temperatures of the compositions at the time of recovery was 27° C. (5 minutes circulation), 29 to 30° C. (10 minutes circulation), and 38 to 39° C. (30 minutes circulation). The composition was allowed to stand for 30 minutes and the large bubbles were degassed.

The compositions after being degassed were further allowed to stand for a predetermined time (0, 1, 2 or 3 hours), and the amount of carbon monoxide contained in the composition after being stand was measured under the measurement conditions of the GC (gas chromatograph) described below. The amount of the carbon monoxide was measured by methanating carbon monoxide and measuring the obtained methane. In addition, the motor 1 was driven for 5 minutes using hydrogen sulfide instead of carbon monoxide, the compositions after being degassed were allowed to stand for a predetermined time (0, 1, 2, 3 or 19 hours), and the amount of hydrogen sulfide contained in the composition was measured under the measurement conditions of the GC described below. It was verified that each composition after a lapse of a predetermined time contains micro bubbles using a laser pointer. The measurement results of carbon monoxide are shown in Table 1 below, and the results of hydrogen sulfide are shown in Table 2 below.

GC Condition (Carbon Monoxide)
  Apparatus: GC-2014 FID (manufactured by Shimadzu Corporation)
  Filler type: MS-13X (Molecular Sieve 13X) (manufactured by GL Sciences Inc.)
  Column type: Shimadzu GC stainless-steel column (inner diameter: 3 mm, length: 3 m, manufactured by Shimadzu Corporation)
Temperature
  Vaporizer: 220° C.
  Column: 50° C.
  Detector: 250° C.
Carrier
  N$_2$ (Nitrogen gas)
  Flow rate: 20 ml/min
  Methanizer: 400° C.
GC Condition (Hydrogen Sulfide)
  Apparatus: GC-2014 FPD (manufactured by Shimadzu Corporation)
  Column Type: 5 rings Shimalite® TPA (Polyphenyl Ether (5 rings) OS-124/Shimalite TPA) (inner diameter: 3.2 mm, length: 3.1 m, manufactured by Shinwa Chemical Industries Ltd.)
Temperature
  Carburetor: 200° C.
Column
  Start temperature: 50° C.
  Retention time at starting temperature: 3 minutes
  Temperature rising rate: 50° C./min
  End temperature: 100° C.
  Retention time at end temperature: 5 minutes
  Detector: 250° C.
Carrier
  N$_2$ (Nitrogen gas)
  Flow rate: 20 ml/min

TABLE 1

| Standing time | 5 minutes circulation | | 10 minutes circulation | | 30 minutes circulation | |
|---|---|---|---|---|---|---|---|
| 0 hours | 142 | 87 | 112 | 24 | 38 | 45 | 4(*) | 7(*) |
| 1 hour | 30 | 36 | 29 | 8(*) | 16(*) | 13(*) | <1(*) | <1(*) |
| 2 hours | 15(*) | 9(*) | 16(*) | <1(*) | 7(*) | <1(*) | N.D. | N.D. |
| 3 hours | 5(*) | 4(*) | <1(*) | N.D. | N.D. | N.D. | N.D. | N.D. |

Unit: μmol/l
(*): below detection limit
N.D.: not detected

TABLE 2

| Standing time | 5 minutes circulation | | |
|---|---|---|---|
| 0 hours | 2200 | 2500 | 2201 |
| 1 hour | 374 | 477 | 414 |
| 2 hours | 105 | 104 | — |
| 3 hours | 14(*) | 19(*) | 6(*) |
| 19 hours | <1(*) | <1(*) | — |

Unit: μmol/l
(*): below detection limit
—: not measured

As shown in Table 1, carbon monoxide in the composition after being stand was rapidly degassed, and the amount of carbon monoxide became substantially below the detection limit after 1 hour. Further, as shown in Table 2, hydrogen sulfide in the composition after being stand was rapidly degassed, and the amount of hydrogen sulfide became substantially below the detection limit after 2 hours.

From these results, since the compositions of Examples 3, 5, 9 to 12 and Reference Example 4 to 9 were allowed to stand for about 2 hours after production and then used, it was found that there was substantially no gas other than micro bubbles, i.e., there was substantially no dissolved gas. Further, since there is no dissolved gas, it was verified that the cell preservation effect, the biomaterial preservation effect, or the like proven in each of Examples and Reference Examples are achieved by the action of the micro bubbles included in the biomaterial preservation composition of the present invention.

Reference Example 2

It was examined that there are micro bubbles in the compositions of Examples 3, 5, 9 to 12 and Reference Example 4 to 9.

A composition used in Reference Example 2 was produced in the same manner as in Reference Example 1 except that 50 ml of physiological saline was used instead of 40 ml of ultrapure water and 10 ml of CO was used instead of 5 ml of CO. The obtained composition was allowed to stand for 30 minutes, the large bubbles were degassed, the resultant was further allowed to stand for a predetermined time (0, 1, 2, 3, 4, 5, or 6 hours), and the density and the mean diameter of the micro bubbles included in the composition after being stand were measured in the same manner as in Reference Example 4 (2) (Reference Example 2-1). The same production and measurement of the composition were performed two more times (Reference Examples 2-2 and 2-3). These results are shown in Table 3 below.

TABLE 3

| Sample | Reference Example 2-1 | | Reference Example 2-2 | | Reference Example 2-3 | |
|---|---|---|---|---|---|---|
| Predetermined time (hour) | Density (bubbles/ml) | Mean diameter (nm) | Density (bubbles/ml) | Mean diameter (nm) | Density (bubbles/ml) | Mean diameter (nm) |
| 0 | $2.95 \times 10^8$ | 115 | $1.25 \times 10^8$ | 99 | $1.63 \times 10^8$ | 123 |
| 1 | $1.25 \times 10^8$ | 153 | $1.26 \times 10^8$ | 104 | $1.64 \times 10^8$ | 135 |
| 2 | $1.02 \times 10^8$ | 174 | $2.58 \times 10^7$ | 143 | $1.60 \times 10^8$ | 147 |
| 3 | $7.26 \times 10^7$ | 180 | $1.00 \times 10^8$ | 110 | $1.33 \times 10^8$ | 151 |
| 4 | $6.84 \times 10^7$ | 196 | $1.03 \times 10^8$ | 117 | $1.23 \times 10^8$ | 153 |
| 5 | — | — | $1.68 \times 10^8$ | 116 | $1.02 \times 10^8$ | 158 |
| 6 | — | — | — | — | $1.05 \times 10^8$ | 165 |

—: not measured

As shown in Table 3, the compositions of Reference Examples 2-1 to 2-3 included about $1 \times 10^8$ bubbles/ml micro bubbles at 1 to 2 hours after being stand. The mean diameter of the micro bubbles at 1 to 2 hours after being stand did not change greatly from the mean diameter of the micro bubbles after the production of the composition. From these results, since the compositions of Examples 3, 5, 9 to 12 and Reference Example 4 to 9 were allowed to stand for about 2 hours after production and then used, it was found that there were about $1 \times 10^8$ bubbles/ml micro bubbles. Further, since the composition included the micro bubbles, it was found that the cell preservation effect, the biomaterial preservation effect, or the like proven in each of Examples and Reference Examples are achieved by the action of the micro bubbles included in the composition of the present invention.

Reference Example 3

It was examined that there was substantially no gas that did not form micro bubbles in the composition including $N_2O$ at 1 hour after production of the composition.

A composition was produced in the same manner as in Reference Example 1 except that the motor 1 was driven for 5 minutes using medical $N_2O$ (Sumitomo Seika Chemicals Co., Ltd., $N_2O$ density: 99.999 (v/v) %) instead of carbon monoxide. After the driving of the motor 1 was stopped, the obtained composition was recovered in a beaker. The temperature of the composition at the time of recovery was 27° C. The composition was allowed to stand for 30 minutes and the large bubbles were degassed.

The compositions after being degassed were further allowed to stand for a predetermined time (0 or 1 hour), and the amount of $N_2O$ contained in the composition after being stand was measured under the measurement conditions of the GC (gas chromatograph) described below (n=3, samples 1 to 3). It was verified that each composition after a lapse of a predetermined time contains micro bubbles using a laser pointer. The results are shown in Table 4 below.

GC Condition ($N_2O$)
  Apparatus: GC-2014 TCD (manufactured by Shimadzu Corporation)
  Filler type: Porapak® Q (manufactured by GL Sciences Inc.)
  Column type: Shimadzu GC stainless-steel column (inner diameter: 3 mm, length: 2 m, manufactured by Shimadzu Corporation)
Temperature
  Vaporizer: 150° C.
  Column: 40° C.
  Detector: 100° C.
Carrier
  He (helium gas)
  Flow rate: 30 ml/min

TABLE 4

| | Sample | | |
|---|---|---|---|
| Standing time | 1 | 2 | 3 |
| 0 hour | 3077 | 2469 | 1941 |
| 1 hour | N.D. | N.D. | N.D. | unit: μ mol/L
N.D.: not detected

As shown in Table 4, $N_2O$ in the composition after being stand was rapidly degassed to a level below the detectable limit in 1 hour. From these results, it was found that, when the composition was allowed to stand for about 1 hour after production and then used, there was substantially no gas other than micro bubbles, i.e., there was substantially no dissolved gas.

While the present invention has been described above with reference to illustrative embodiments, the present invention is by no means limited thereto. Various changes and variations that may become apparent to those skilled in the art may be made in the configuration and specifics of the present invention without departing from the scope of the present invention.

This application claims priority from Japanese Patent Application No. 2018-105405 filed on May 31, 2018 and Japanese Patent Application No. 2018-226902 filed on Dec. 3, 2018. The entire subject matter of the Japanese Patent Applications is incorporated herein by reference.

SUPPLEMENTARY NOTES

Some or all of the above embodiments and examples may be described as in the following Supplementary Notes, but are not limited thereto.
(Supplementary Note 1)
  A biomaterial preservation composition including a micro bubble.
(Supplementary Note 2)
  The biomaterial preservation composition according to Supplementary Note 1, wherein the micro bubble contains at least one selected from the group consisting of hydrogen ($H_2$), nitrogen monoxide (NO), nitrous oxide ($N_2O$), carbon monoxide (CO), carbon dioxide ($CO_2$), hydrogen sulfide ($H_2S$), oxygen ($O_2$), ozone ($O_3$), helium (He), argon (Ar), krypton (Kr), xenon (Xe), nitrogen ($N_2$), air, methane ($CH_4$), ethane ($CH_3CH_3$), propane ($CH_3CH_2CH_3$), fluoromethane ($CH_3F$), difluoromethane ($CH_2F_2$), carbon tetrafluoride ($CF_4$), and ethylene oxide ($C_2H_4O$).

(Supplementary Note 3)

The biomaterial preservation composition according to Supplementary Note 1 or 2, wherein the micro bubble contains a biological gas as a gas.

(Supplementary Note 4)

The biomaterial preservation composition according to any one of Supplementary Notes 1 to 3, wherein
the micro bubble contains at least one of carbon monoxide (CO) or hydrogen sulfide ($H_2S$) as a gas.

(Supplementary Note 5)

The biomaterial preservation composition according to Supplementary Note 4, wherein the micro bubble contains oxygen as a gas.

(Supplementary Note 6)

The biomaterial preservation composition according to any one of Supplementary Notes 1 to 5, wherein
the micro bubble has a density of $5 \times 10^5$ to $5 \times 10^{12}$ bubbles/ml.

(Supplementary Note 7)

The biomaterial preservation composition according to any one of Supplementary Notes 1 to 6 further including:
a medium, wherein
the medium is at least one of a liquid or a solid.

(Supplementary Note 8)

A method for preserving a biomaterial, including the step of:
preserving a biomaterial in a presence of a micro bubble.

(Supplementary Note 9)

The method for preserving a biomaterial according to Supplementary Note 8, wherein
the micro bubble includes the micro bubble in the biomaterial preservation composition according to any one of Supplementary Notes 1 to 7.

(Supplementary Note 10)

The method for preserving a biomaterial according to Supplementary Note 8 or 9, further including the step of:
perfusing the biomaterial with a liquid containing the micro bubbles.

(Supplementary Note 11)

The method for preserving a biomaterial according to any one of Supplementary Notes 8 to 10, wherein
the biomaterial includes at least a part of a living body or an organ.

(Supplementary Note 12)

The method for preserving a biomaterial according to Supplementary Note 11, wherein the part of the living body includes at least one selected from the group consisting of a limb, a finger, a face, a bone, a muscle, a hair root, a tooth, and a periodontal membrane.

(Supplementary Note 13)

The method for preserving a biomaterial according to Supplementary Note 11, wherein
the organ includes at least one selected from the group consisting of an eyeball, a cornea, a lung, a heart, a liver, a kidney, a spleen, a pancreas, a gall bladder, an esophagus, a stomach, a small intestine, a large intestine, a testis, an ovary, a central nervous system, a peripheral nervous system, a blood vessel, and skin.

(Supplementary Note 14)

A method for preserving a biomaterial, including the steps of:
introducing a micro bubble into a biomaterial; and preserving the biomaterial.

(Supplementary Note 15)

The method for preserving a biomaterial according to Supplementary Note 14, wherein the micro bubble includes the micro bubble in the biomaterial preservation composition according to any one of Supplementary Notes 1 to 7.

(Supplementary Note 16)

The method for preserving a biomaterial according to Supplementary Note 14 or 15, wherein
in the preserving step, a biomaterial is preserved in a presence of a micro bubble.

(Supplementary Note 17)

The method for preserving a biomaterial according to Supplementary Note 16, wherein the micro bubble includes the micro bubble in the biomaterial preservation composition according to any one of Supplementary Notes 1 to 7.

(Supplementary Note 18)

The method for preserving a biomaterial according to any one of Supplementary Notes 14 to 17, wherein
the biomaterial includes at least a part of a living body or an organ.

(Supplementary Note 19)

The method for preserving a biomaterial according to Supplementary Note 18, wherein the part of the living body includes at least one selected from the group consisting of a limb, a finger, a face, a bone, a muscle, a hair root, a tooth, and a periodontal membrane.

(Supplementary Note 20)

The method for preserving a biomaterial according to Supplementary Note 18, wherein
the organ includes at least one selected from the group consisting of an eyeball, a cornea, a lung, a heart, a liver, a kidney, a spleen, a pancreas, a gall bladder, an esophagus, a stomach, a small intestine, a large intestine, a testis, an ovary, a central nervous system, a peripheral nervous system, a blood vessel, and skin.

(Supplementary Note 21)

A method for producing a biomaterial, including the step of:
preserving a produced biomaterial, wherein
the material preserving step is performed by the method for preserving a biomaterial according to any one of Supplementary Notes 8 to 20.

(Supplementary Note 22)

A transplantation material produced by the method for producing a biomaterial according to Supplementary Note 21.

(Supplementary Note 23)

A method of transplantation, including the step of:
transplanting the transplantation material according to Supplementary Note 22 into an animal.

(Supplementary Note 24)

A micro bubble density improver, including a surfactant as an active ingredient.

INDUSTRIAL APPLICABILITY

As described above, according to the present invention, cells can be preserved. In addition, the present invention can suppress a decrease in viability of cells during cell preservation, for example. For this reason, the present invention is significantly useful, for example, in the life science field, the medical field, the pharmaceutical field, and the like, in which cell preservation, cell culture, and the like are performed.

The invention claimed is:

1. A biomaterial preservation composition comprising a microbubble in a liquid, wherein the micro bubble comprises (i) oxygen ($O_2$) gas, and (ii) at least one of carbon monoxide (CO) gas and hydrogen sulfide ($H_2S$) gas, wherein the gas of the micro bubble directly contacts with the liquid;

wherein the micro bubble density is $6.84 \times 10^5$ to $5 \times 10^{12}$ bubbles/ml;

wherein the mean diameter of the bubbles is less than 1 μm; and wherein the biomaterial comprises at least a part of a living body or an organ.

2. The biomaterial preservation composition according to claim 1, wherein the micro bubble further contains at least one selected from the group consisting of hydrogen ($H_2$), nitrogen monoxide (NO), nitrous oxide ($N_2O$), carbon dioxide ($CO_2$), ozone ($O_3$), helium (He), argon (Ar), krypton (Kr), xenon (Xe), nitrogen ($N_2$), air, methane ($CH_4$), ethane ($CH_3CH_3$), propane ($CH_3CH_2CH_3$), fluoromethane ($CH_3F$), difluoromethane ($CH_2F_2$), carbon tetrafluoride ($CF_4$), and ethylene oxide ($C_2H_4O$).

3. The biomaterial preservation composition according to claim 1, wherein the micro bubble contains the carbon monoxide (CO) gas and the hydrogen sulfide ($H_2S$) gas.

4. The biomaterial preservation composition according to claim 1, wherein the micro bubble contains carbon monoxide (CO) gas and oxygen ($O_2$) gas.

5. The biomaterial preservation composition according to claim 1, wherein the micro bubble contains hydrogen sulfide ($H_2S$) gas and oxygen ($O_2$) gas.

6. The biomaterial preservation composition according to claim 4, wherein a volume ratio of the carbon monoxide (CO) gas and the oxygen ($O_2$) in the micro bubble is between 1.5:8.5 and 3:7.

7. The biomaterial preservation composition according to claim 1, wherein the liquid is selected from the group consisting of water, an aqueous solvent, an oily solvent, a physiological saline, a preservative solution, an extracellular solution or infusion, and a mixed solvent thereof.

* * * * *